United States Patent
Shigematsu et al.

(10) Patent No.: US 6,671,392 B1
(45) Date of Patent: Dec. 30, 2003

(54) FINGERPRINT RECOGNITION APPARATUS AND DATA PROCESSING METHOD

(75) Inventors: Satoshi Shigematsu, Kanagawa (JP); Hiroki Morimura, Kanagawa (JP); Katsuyuki Machida, Kanagawa (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 09/472,392

(22) Filed: Dec. 23, 1999

(30) Foreign Application Priority Data

Dec. 25, 1998 (JP) .......................... 10-370934
Sep. 13, 1999 (JP) .......................... 11-258533

(51) Int. Cl.[7] .............................. G06K 9/00
(52) U.S. Cl. ........................................ 382/124
(58) Field of Search ................. 382/115–124; 235/380, 382, 382.5; 902/3–6; 713/182, 186; 340/5.53, 5.83

(56) References Cited

U.S. PATENT DOCUMENTS

| 4,429,413 A | 1/1984 | Edwards |
| 6,392,636 B1 * | 5/2002 | Ferrari et al. ............... 345/173 |

FOREIGN PATENT DOCUMENTS

| JP | 61-221883 | 10/1986 |
| JP | 63-310087 | 12/1988 |
| JP | 1-223576 | 9/1989 |
| JP | 1-310467 | 12/1989 |
| JP | 3-269780 | 12/1991 |
| JP | 4-096824 | 3/1992 |
| JP | 4-332089 | 11/1992 |
| JP | 5-061965 | 3/1993 |
| JP | 5-324806 | 12/1993 |
| JP | 7-168930 | 7/1995 |
| JP | 7-271977 | 10/1995 |
| JP | 9-106456 | 4/1997 |

OTHER PUBLICATIONS

A Study on the Structure of a Smart Card with the Function to verify the Holder Technical Report of IEICE, OSF92–32, pp. 25–30 11/92.

* cited by examiner

*Primary Examiner*—Samir Ahmed
*Assistant Examiner*—Vikkram Bali
(74) *Attorney, Agent, or Firm*—Blakely, Sokoloff, Taylor & Zafman

(57) ABSTRACT

The fingerprint recognition apparatus of this invention has a plurality of pixel units. Each pixel unit has a fingerprint sensor circuit including a sensor element for converting a three-dimensional pattern of a skin surface of a finger coming into contact with the element into an electrical signal, and a sensor circuit for processing the electrical signal converted by the sensor element and outputting predetermined data. Each pixel unit also has a fingerprint memory in which user's registered fingerprint data and a recognition circuit for collating the fingerprint data detected by the fingerprint sensor circuit with the registered fingerprint data. A control circuit controls the pixel units and totalizes recognition results.

25 Claims, 22 Drawing Sheets

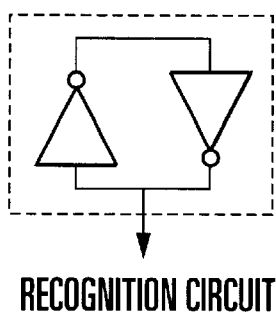
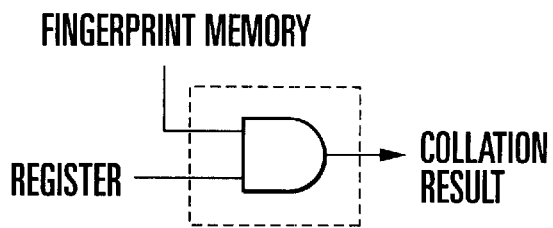
FIG. 4    FIG. 5
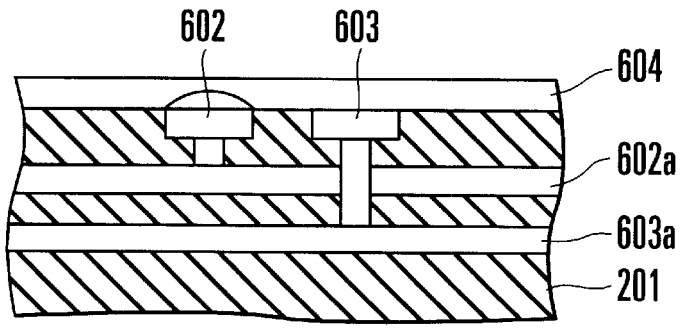
FIG. 6
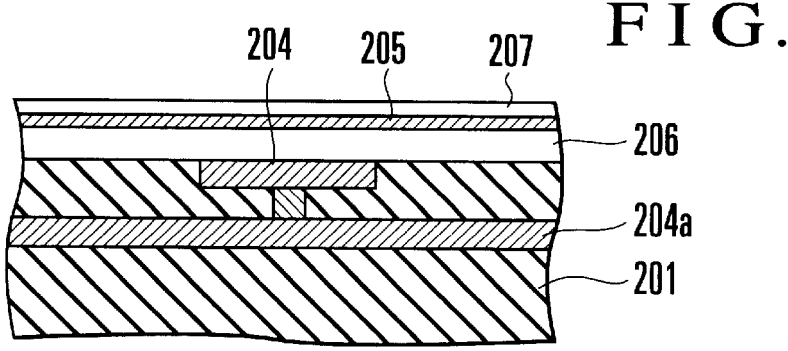
FIG. 7
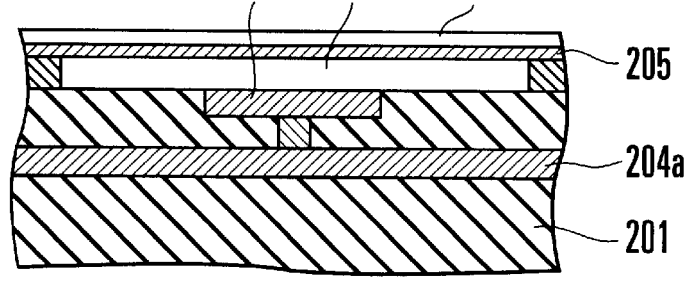
FIG. 8

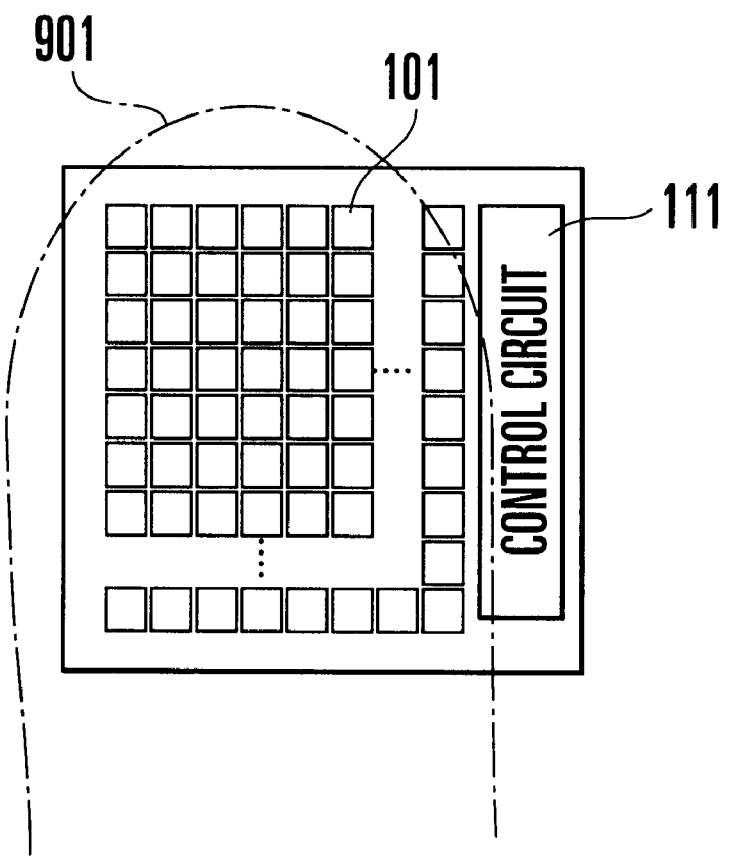
F I G. 9

⇩ LEFT SHIFT

⇩ LEFT SHIFT

⇩ RIGHT SHIFT

FINGERPRINT RECOGNITION APPARATUS AND DATA PROCESSING METHOD

BACKGROUND OF THE INVENTION

The present invention relates to a fingerprint recognition apparatus and, more particularly, to a fingerprint recognition apparatus in which a sensor for detecting a fingerprint pattern is formed on an integrated circuit for recognizing the fingerprint to perform both detection and recognition of the fingerprint, and a data processing method.

In the social environment of today where an information-oriented society is progressing, the security technology has taken a growing interest. For example, in the information-oriented society, a personal verification technology for constructing, e.g., an electronic money system is an important key. In fact, verification technologies for implementing preventive measures against burglary and illicit use of cards are under active research and development (Yoshimasa Shimizu, "A Study on the Structure of a Smart Card with the Function to Verify the Holder", Technical Report of IEICE, OFS92-32, pp. 25–30, November 1992).

A variety of verification schemes use a fingerprint or voiceprint for preventive measures against illicit use. Especially for fingerprint verification, many techniques have conventionally been developed. Fingerprint verification schemes are roughly classified into optical reading schemes and schemes of converting the three-dimensional pattern of a skin surface into an electrical signal and detecting it using human electrical characteristics.

In an optical reading scheme, a fingerprint is received as optical image data and collated mainly using reflection of light and a CCD image sensor (Japanese Patent Laid-Open No. 61-221883). Another scheme uses a piezoelectric thin film to read the pressure difference in the fingerprint pattern of a finger (Japanese Patent Laid-Open No. 5-61965). As a similar scheme of replacing a change in electrical characteristics caused by the touch of a skin into an electrical signal distribution and detecting a fingerprint pattern, a verification scheme of detecting an amount of change in resistance or capacitance using a pressure sensitive sheet has been proposed (Japanese Patent Laid-Open No. 7-168930).

However, of the above techniques, the scheme using light is hard to form a compact device, and use for a general purpose is also difficult, resulting in limited application purposes. The scheme of detecting the three-dimensional pattern of the skin surface of a finger using a pressure sensitive sheet or the like is hardly put into practical use and poor in reliability because of special materials and low workability.

A conventional fingerprint reading apparatus is separated from a fingerprint recognition apparatus. A fingerprint sensor for detecting a fingerprint pattern must output read fingerprint data externally from the reading apparatus. To do this, a method of scanning data detected by each pixel unit of a fingerprint sensor and externally outputting the data can be used (e.g., Teruhiko Tamori, Japanese Patent Laid-Open No. 63-310087). However, in this method, fingerprint data is output in units of data corresponding to pixel units. For this reason, when the number of pixel units of the fingerprint sensor increases, a long time (e.g., several sec) is required to output all fingerprint data. If a long time is necessary, quick fingerprint recognition of a user may be difficult.

In fingerprint recognition, the fingerprint image obtained by the fingerprint sensor must be collated with user fingerprint data registered in advance. For fingerprint collation, a feature point of the fingerprint image is extracted and compared with a registered feature point, or the fingerprint image is directly collated with a registered image. To realize the collation method, conventionally, a fingerprint recognition apparatus constructed by a microprocessor or the like is used. In the above fingerprint recognition method, processing such as generation or search of feature points or image matching ratio detection, which requires a large amount of calculation, must be performed. Hence, a high-performance processor is required to result in an expensive fingerprint recognition system. This can hardly be applied to a device such as an IC card or portable device requiring low cost.

When a fingerprint recognition system is constructed using a fingerprint reading apparatus and fingerprint recognition apparatus, a conventional fingerprint recognition system comprises a fingerprint reading apparatus 301 for obtaining a fingerprint, a fingerprint recognition apparatus 303 for collating the read fingerprint with fingerprint data in a database 302 where user fingerprint data are registered, and a processing apparatus 304 for performing processing on the basis of the recognition result, as shown in FIG. 33. In the arrangement shown in FIG. 33, the apparatuses are separated from each other. For this reason, the system allows alteration of information during data transfer between the apparatuses and consequently illicit recognition. In the arrangement shown in FIG. 33, since the apparatuses are separated, the entire fingerprint recognition system becomes bulky and can hardly be applied to a small device such as an IC card or portable device.

For collation at a higher speed, recognition apparatuses may be parallelly operated (e.g., Akihiro Nomura, fingerprint collation processing apparatus, Japanese Patent Laid-Open No. 7-271977). In this method, however, a plurality of conventional recognition apparatuses are used to recognize a fingerprint by pipeline parallel operation. Although the processing time can be shortened, the scale of the apparatus becomes large, and cost reduction and application to a portable device are difficult.

For a personal recognition system using an IC card, a method of holding data prepared from a user's fingerprint not in a database but in an IC card and using this data for recognition as registered data of the user has been proposed (e.g., Shinji Oki, personal confirmation method for use of a card, personal confirmation system using an IC card, and IC card used for this system, Japanese Patent Application No. 9-106456). In this method as well, a memory (in this case, an IC card) for holding registered fingerprint data, fingerprint reading apparatus, and recognition apparatus are separated from each other, as in the above method. Hence, leakage of personal data from the IC card, leakage of data at the time of recognition, or alteration may occur. To recognize a fingerprint, the fingerprint reading apparatus and fingerprint recognition apparatus are necessary in addition to the IC card. Fingerprint recognition in use of the IC card is impossible without these apparatuses.

SUMMARY OF THE INVENTION

It is therefore the principal object of the present invention to apply a fingerprint recognition system that is difficult to alter fingerprint data to a compact device such as an IC card or portable device at low cost.

In order to achieve the above object, according to an aspect of the present invention, a fingerprint recognition apparatus comprises a plurality of pixel units each having a sensor element for converting a three-dimensional pattern of a skin surface of a finger coming into contact with the sensor element into an electrical signal, a sensor circuit for processing the electrical signal converted by the sensor element and outputting predetermined data, a fingerprint memory in which fingerprint data representing the three-dimensional pattern of the skin surface of the finger is registered in advance, and an arithmetic circuit for collating the data output from the sensor circuit with the fingerprint data in the fingerprint memory and outputting a collation result.

According to the present invention with this arrangement, both reading and recognition of a fingerprint at the pixel unit portion can be performed in one pixel unit.

BRIEF DESCRIPTION OF THE DRAWINGS

FIG. 4 is a view showing a partial arrangement of the pixel unit according to the first embodiment of the present invention;

FIG. 5 is a view showing a partial arrangement of the pixel unit according to the first embodiment of the present invention;

FIG. 6 is a sectional view schematically showing another structure of the sensor element according to the first embodiment of the present invention;

FIG. 7 is a sectional view schematically showing still another structure of the sensor element according to the first embodiment of the present invention;

FIG. 8 is a sectional view schematically showing still another structure of the sensor element according to the first embodiment of the present invention;

FIG. 9 is an explanatory view showing the relationship between a finger and the fingerprint recognition apparatus of the present invention;

DESCRIPTION OF THE PREFERRED EMBODIMENTS

The embodiments of the present invention will be described below with reference to the accompanying drawings.

First Embodiment

Figure 1A:
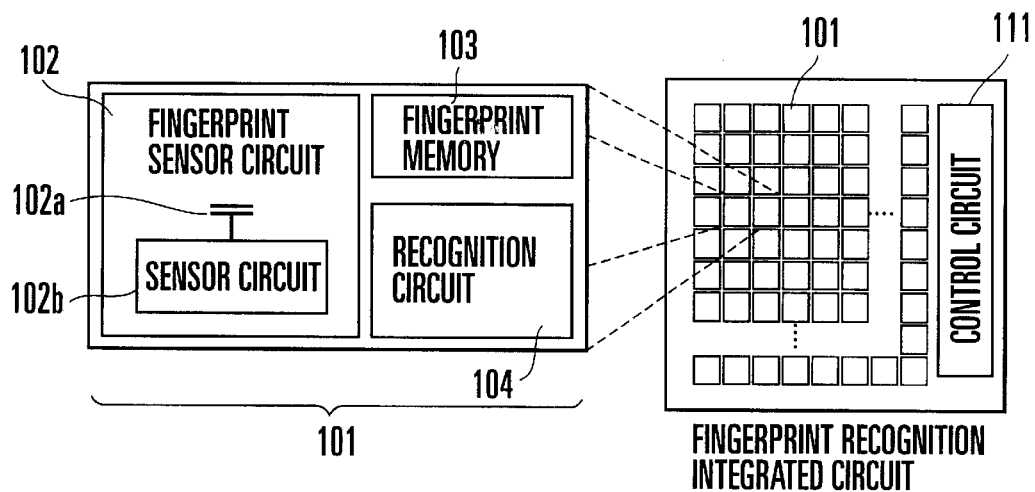
FIGS. 1A and 1B are views showing the structure of a fingerprint recognition apparatus according to the first embodiment of the present invention.

The first embodiment of the present invention will be described first. A fingerprint recognition apparatus according to the first embodiment constitutes a pixel unit array by arraying a plurality of pixel units 101 in a matrix, as shown in FIG. 1A.

Each pixel unit 101 has a fingerprint sensor circuit 102 for detecting a fingerprint pattern, which comprises a sensor element 102a for converting the three-dimensional pattern of the skin surface of a finger (not shown) coming into contact with the element into an electrical signal and a sensor circuit 102b for processing the electrical signal converted by the sensor element 102a and outputting predetermined data. The pixel unit 101 also has a fingerprint memory 103 holding the registered fingerprint of a user and a recognition circuit 104 for collating the fingerprint data detected by the fingerprint sensor circuit 102 with the registered fingerprint data. A control circuit 111 controls each pixel unit 101 and totalizes recognition results.

The registered fingerprint data of the user is divisionally stored in the fingerprint memories 103 of the pixel units 101. The fingerprint pattern of a finger placed on the fingerprint recognition apparatus shown in FIG. 1A is converted into electrical signals by the fingerprint sensor circuits 102 of all pixel units 101. The recognition circuit 104 performs signal processing using the electrical signal (data) representing the fingerprint pattern, which is converted by the fingerprint sensor circuit 102, and the registered fingerprint data in the fingerprint memory 103 and outputs the recognition result.

The recognition results from all the pixel units 101 are totalized by the control circuit 111. The control circuit 111 generates a recognition result on the basis of the totalized results and externally outputs the generated result. The above processing operations can be simultaneously ultra-parallelly performed. This parallel processing shortens the recognition processing time and reduces power consumption. When each pixel unit 101 has a plurality of sensor circuits and a plurality of fingerprint memories per recognition circuit and selectively uses the fingerprint sensor circuits and fingerprint memories in accordance with a control signal from the control circuit, the area can be reduced. Each fingerprint sensor circuit may have a plurality of sensor elements.

Figure 1B:
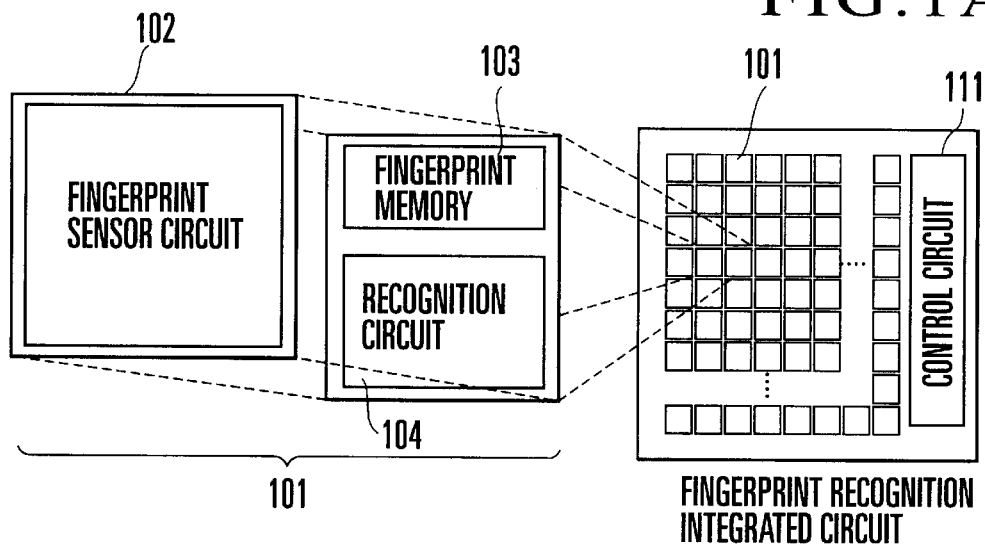
Figure 1C:
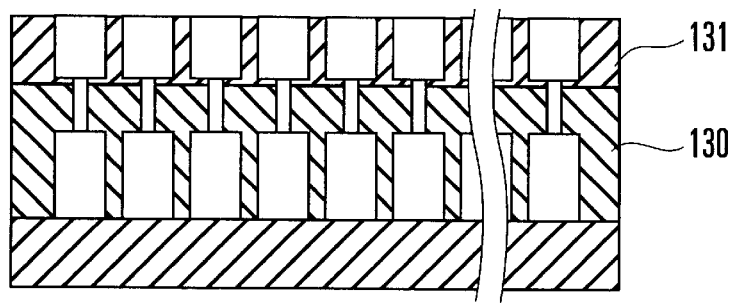
FIG. 1C is a sectional view showing a partial structure of the fingerprint recognition apparatus according to the first embodiment of the present invention.

In the pixel unit 101, the verification circuit portion, including the fingerprint memory 103 and recognition circuit 104, and the fingerprint sensor circuit 102 are divisionally formed in a logic circuit layer 130 and sensor layer 131, respectively, on a substrate 140 in a stacked manner, as shown in FIGS. 1B and 1C. This increases the degree of integration of the pixel units.

Figure 2:
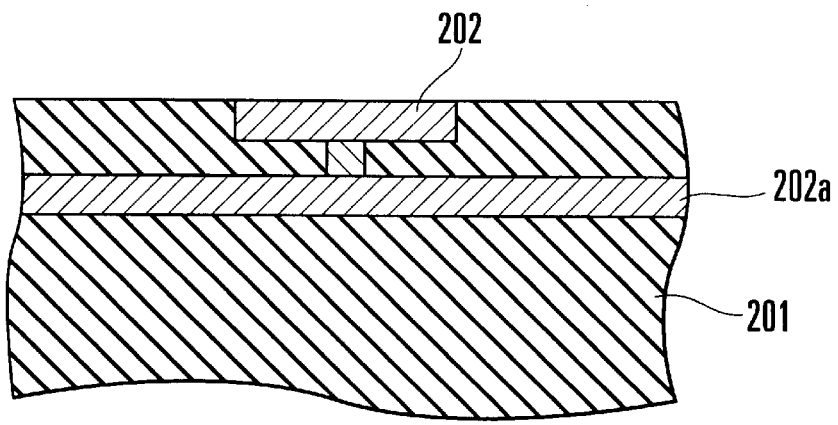
FIG. 2 is a sectional view schematically showing a structure of a sensor element according to the first embodiment of the present invention.

The sensor element in the fingerprint sensor circuit formed in the sensor layer is constructed by a contact electrode 202 formed on an interlevel insulator 201 and an interconnection 202a connected to the contact electrode 202, so the contact electrode 202 and interconnection 202a form part of the fingerprint sensor circuit, as shown in FIG. 2. The contact electrode 202 is formed on the uppermost surface of the pixel unit. When a finger as a fingerprint recognition object directly touches the contact electrode 202, the contact electrode 202 detects an electrostatic capacitance generated by the touch of the finger. The signal detected by the contact electrode 202 is sent to the recognition circuit via the interconnection 202a. Since the structure shown in FIG. 2 is very simple and can be micropatterned, the resolution of data of the detected fingerprint can be improved.

Figure 3:
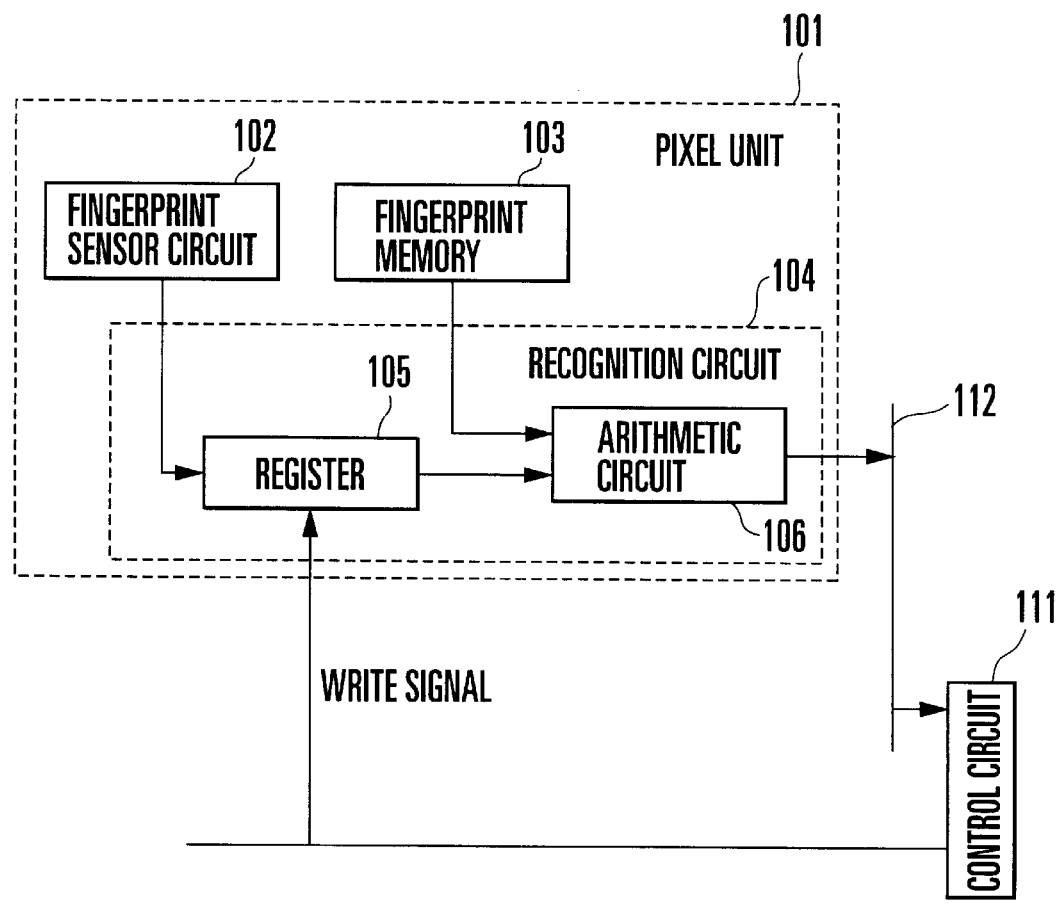
FIG. 3 is a view showing the arrangement of a pixel unit according to the first embodiment of the present invention.

This will be described in more detail. The recognition circuit 104 has a register (holding means) 105 for holding the output from the fingerprint sensor circuit 102 and an arithmetic circuit 106 for performing logical calculation including collation between the output from the register 105 and the output from the fingerprint memory 103, as shown in FIG. 3. The arithmetic circuits 106 of the respective pixel units 101 output the calculation results (recognition results) to a data bus 112 such that the control circuit 111 can totalize them. The control circuit 111 which totalizes the recognition results also generates a write signal for the register 105 in the recognition circuit 104. When a plurality of pixel units 101 are arranged and connected to the control circuit 111 through the data bus 112, a fingerprint recognition apparatus which performs both detection and recognition of a fingerprint is realized.

As shown in FIG. 4, the fingerprint memory 103 can be realized by a simple inverter element. The circuit shown in FIG. 4 can hold fingerprint data of one bit. When the capacity is increased, fingerprint data of a plurality of fingers or a plurality of persons can be held. The arithmetic circuit 106 can be realized by, e.g., an AND element shown in FIG. 5.

In this embodiment, the sensor element has one contact electrode. However, the present invention is not limited to this. For example, as shown in FIG. 6, a light-emitting element 602 and light-receiving element 603 are formed on the interlevel insulator 201, which are protected by a transparent protective film 604. A power for light emission is supplied to the light-emitting element 602 through an interconnection 602a. The light-receiving element 603 is connected to he recognition circuit (not shown) arranged underneath the interlevel insulator 201 through an interconnection 603a. This sensor element optically detects the three-dimensional pattern of the skin surface of a finger by the light-receiving element 603 using the light-emitting element 602 as a light source.

As shown in FIG. 7, a lower electrode 204 and an upper electrode 205 which is separately formed above the lower electrode 204 may be formed on the interlevel insulator 201. The space between the upper electrode 205 and the lower electrode 204 is filled with a cushioning material 206, and the upper electrode 205 is protected by a protective film 207. When the three-dimensional pattern of the skin surface of a finger touches the surface of the sensor element (the surface of the protective film 207) shown in FIG. 7, the upper electrode 205 bends in accordance with the shape of the three-dimensional pattern, so the interval between the upper electrode 205 and the lower electrode 204 changes. When the interval changes due to the touch of the three-dimensional pattern of the skin surface of the finger, the capacitance on the lower electrode 204 also changes. When the change in capacitance on the lower electrode 204 is detected and measured by the recognition circuit connected to the lower electrode 204 through an interconnection 204a, the three-dimensional pattern of the skin surface of the finger in contact with the fingerprint sensor circuit with this sensor element can be detected.

As shown in FIG. 8, in the structure of the sensor element shown in FIG. 7, the cushioning material 206 between the lower electrode 204 and the upper electrode 205 may be removed, and a space 206a may be formed between the lower electrode 204 and the upper electrode 205.

Second Embodiment

The second embodiment of the present invention will be described next.

In this fingerprint recognition apparatus, when a finger is placed on a fingerprint recognition area where pixel units are arrayed in a matrix, the fingerprint pattern of the placed finger is compared with data stored in the fingerprint memory in units of pixel units. The fingerprint recognition area recognizes not the entire fingerprint of a finger 901 but a partial area of the fingerprint, as shown in FIG. 9. If the entire fingerprint area is to be recognized, the fingerprint recognition apparatus becomes bulky. For this reason, the recognition area is made small within the range capable of fingerprint recognition. Under this circumstance, the fingerprint memory stores data when the fingerprint recognition area and the finger have a predetermined positional relationship therebetween. When the position of the finger with respect to the fingerprint recognition area is different from that by the data stored in the fingerprint memory, fingerprint recognition cannot be accurately performed.

To prevent this, in the second embodiment, detected fingerprint data is shifted to the upper, lower, left, or right pixel unit, as will be described below.

Figure 10:
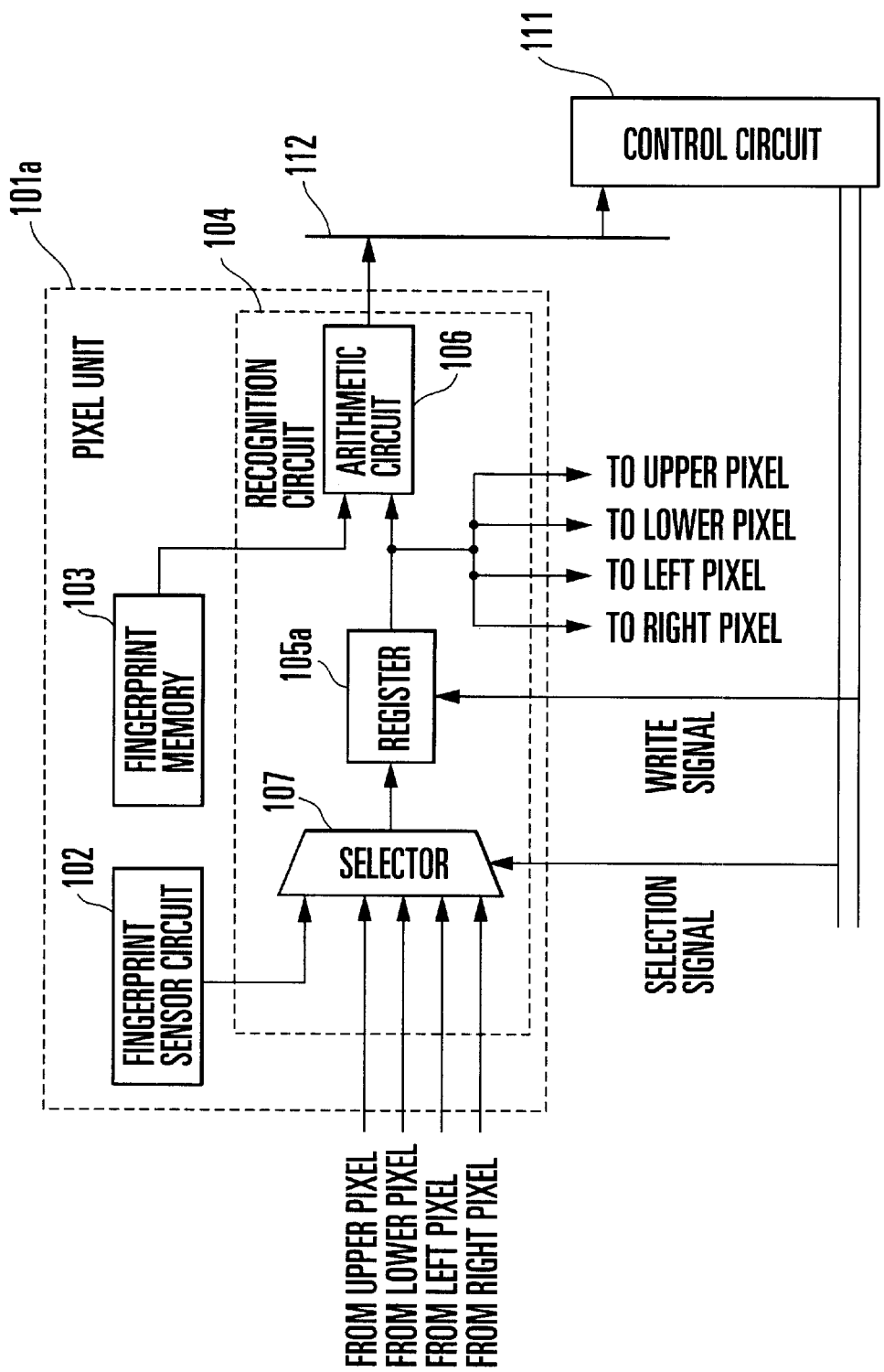
FIG. 10 is a view showing the arrangement of a pixel unit according to the second embodiment of the present invention.
Figure 11:
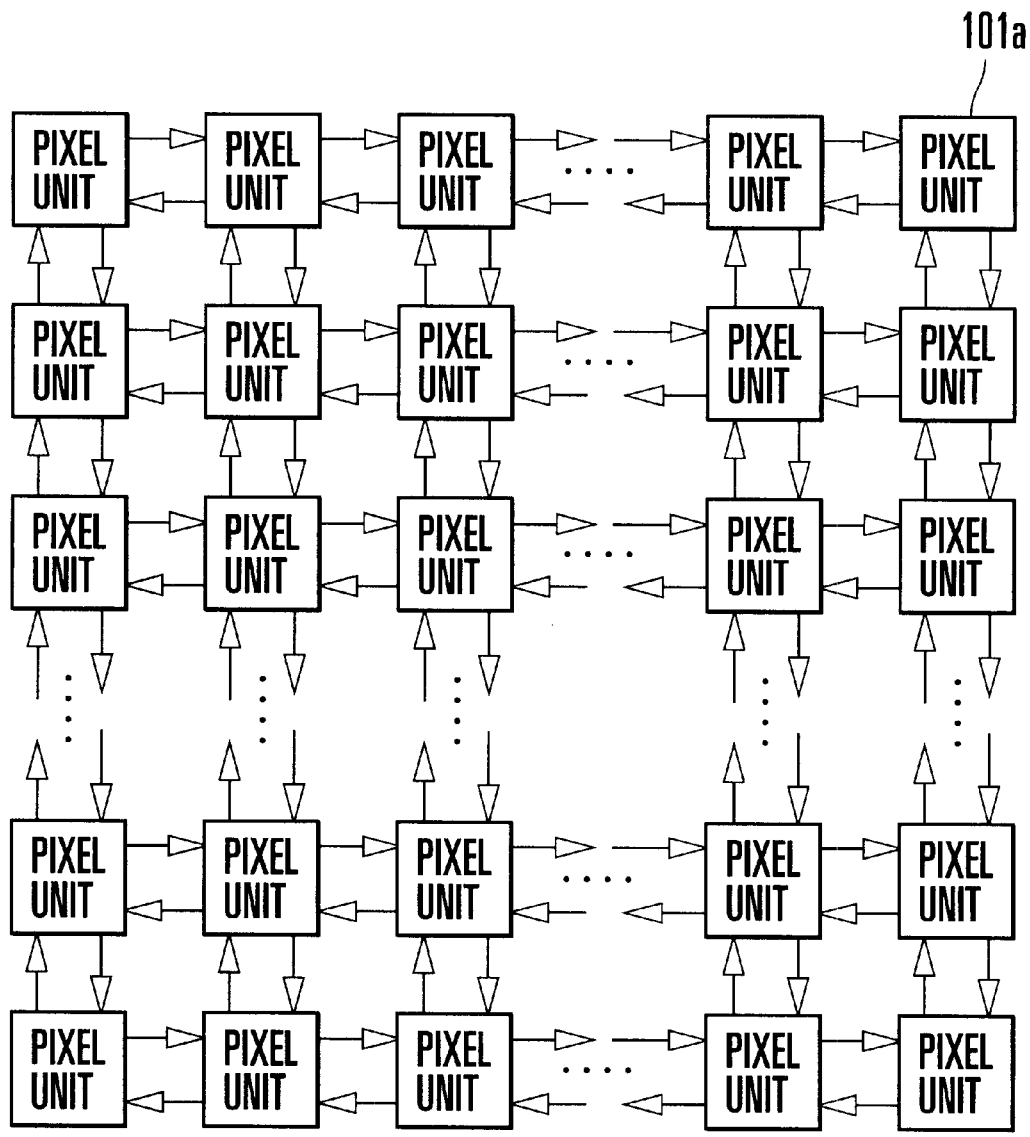
FIG. 11 is a plan view schematically showing the layout of pixel units according to the second embodiment of the present invention.

In the fingerprint recognition apparatus of this embodiment, a pixel unit 101a having the structure shown in FIG. 10 is used in place of each pixel unit 101 of the fingerprint recognition apparatus shown in FIG. 1A, and the pixel units 101a are connected as shown in FIG. 11.

The structure of the pixel unit 101a will be described. In this embodiment, a selector 107 is newly provided in each pixel unit. Each pixel unit also has a register (holding/transfer means) 105a for holding the signal (data) output from a fingerprint sensor circuit 102 and outputting (transmitting) this data to the selectors of the upper, lower, left, or right pixel unit. Hence, the selector 107 of each pixel unit 101a receives register outputs from the upper, lower, left, and right pixel units together with the signal from the fingerprint sensor circuit 102. In this embodiment, a control circuit 111 outputs a write signal to the register 105a and a selection signal to the selector 107.

In the pixel unit shown in FIG. 10 as well, fingerprint data detected and converted by the fingerprint sensor circuit 102 is held by the register 105a through the selector 107 in the initial step (fingerprint detection step). In this initial step, the selector 107 connects the signal from the fingerprint sensor circuit 102 to the register 105a in accordance with the selection signal from the control circuit 111. In this embodiment, after the fingerprint data is held by the register 105a, the control circuit 111 controls the selector 107 with the selection signal to select fingerprint data from another pixel unit. The selected fingerprint data is output to the register 105a. Under the control of the control circuit 111, the register 105a holds fingerprint data detected by the fingerprint sensor circuit of, e.g., the pixel unit adjacent on the left side, unlike in the initial detection step. That is, detected data is shifted to the upper, lower, left, or right pixel unit in accordance with the selection signal from the control circuit 111. According to this embodiment, the fingerprint data detected in the initial step can be shifted to the desired one of upper, lower, left, and right directions under the control of the control circuit 111. This shift enables correction of the offset between the position of fingerprint data detected by the fingerprint sensor circuit 102 and that of fingerprint data held in a fingerprint memory 103, resulting in improvement of the verification ratio.

Third Embodiment

The third embodiment of the present invention will be described next.

Figure 12:
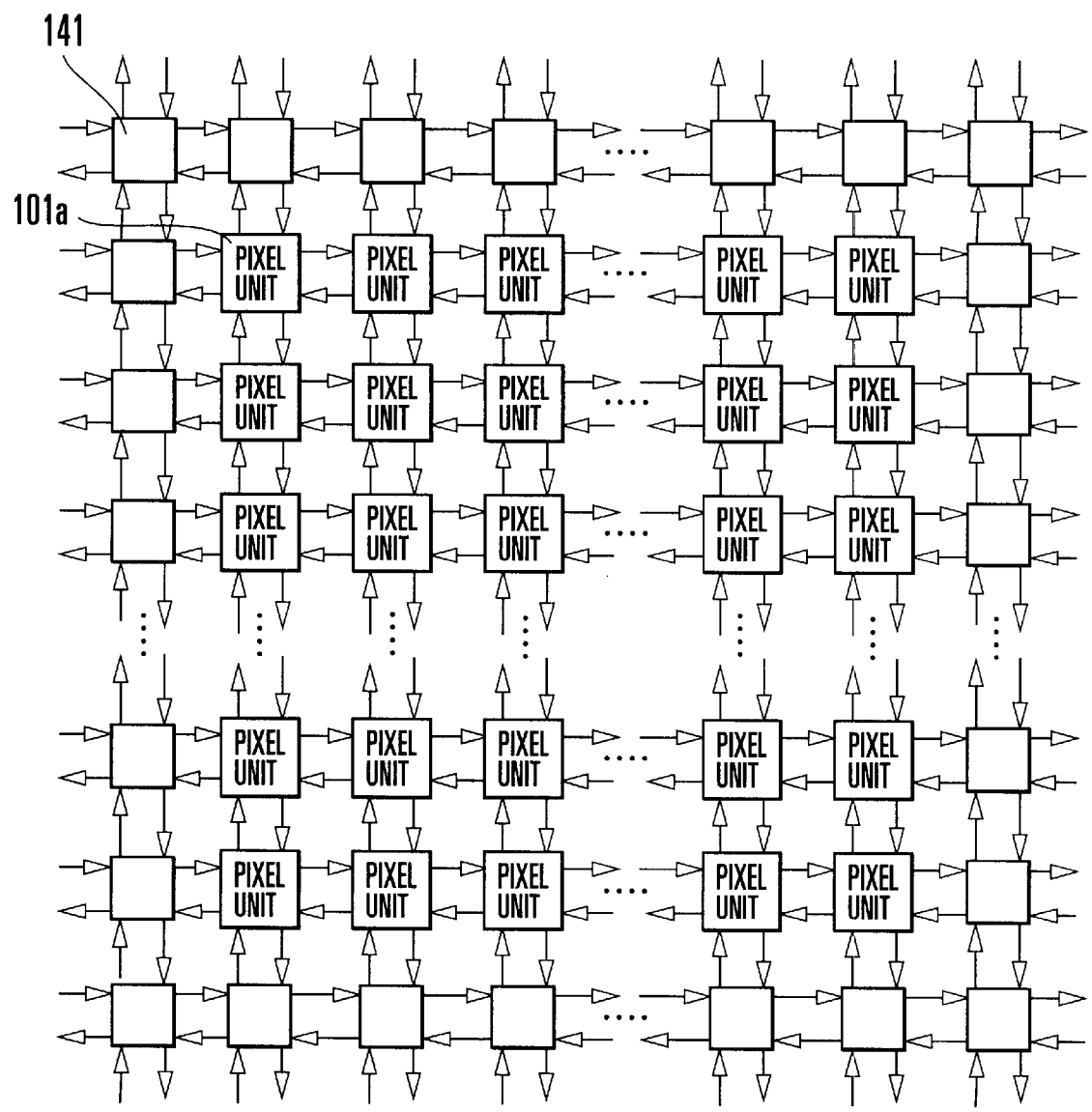
FIG. 12 is a plan view schematically showing the layout of pixel units according to the third embodiment of the present invention.

In the fingerprint recognition apparatus according to the third embodiment, buffer units 141 are arranged around the pixel unit array formed from pixel units 101a arranged in a matrix as if pixel units are added to the pixel unit array. The buffer units 141 are connected to the outermost pixel units 101a of the pixel unit array, as shown in FIG. 12.

Figure 13:
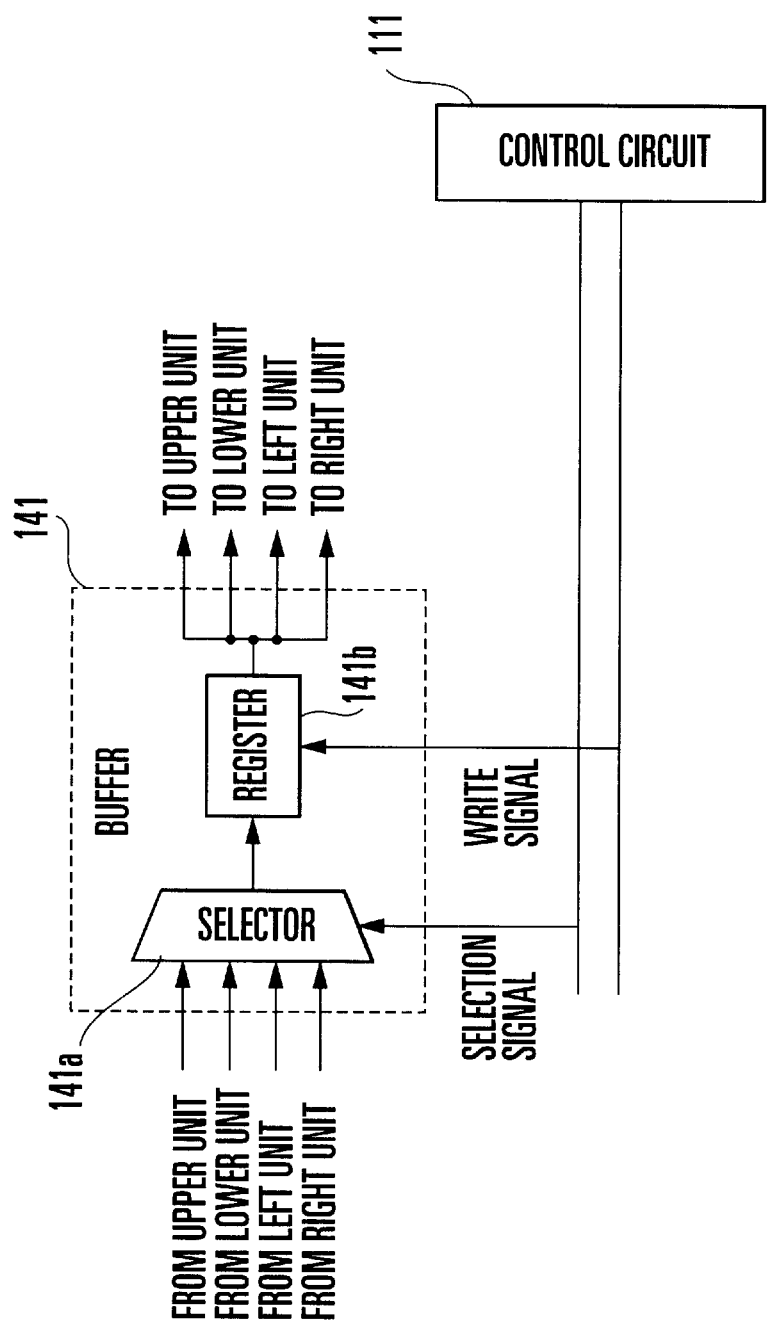
FIG. 13 is a plan view schematically showing the arrangement of a buffer unit according to the third embodiment of the present invention.

The buffer unit 141 will be described. As shown in FIG. 13, the buffer unit 141 has a selector 141a and register 141b operating in accordance with signals like the selection signal to the selector and the write signal to the register in each pixel unit, which are generated by a control circuit 111. When the buffer units 141 are arranged around the pixel unit array of pixel units and connected to the upper, lower, left, and right units, data that stretch out from the pixel unit array can be held. Hence, omission of data when shifting the data can be prevented.

Fourth Embodiment

The fourth embodiment of the present invention will be described next.

Figure 14:
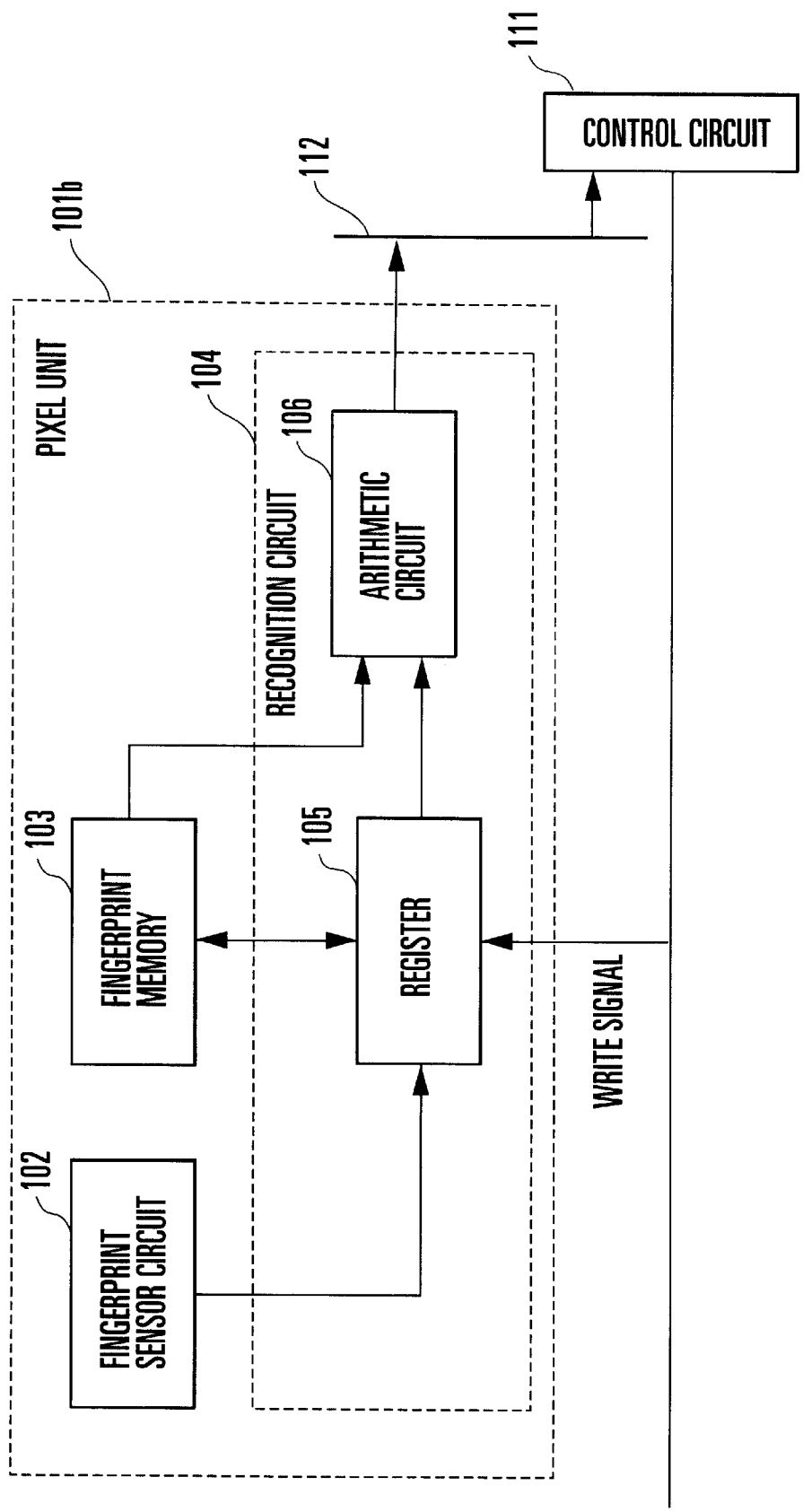
FIG. 14 is a view showing an arrangement of a pixel unit according to the fourth embodiment of the present invention.

In the fingerprint recognition apparatus of the fourth embodiment, as pixel units 101 arrayed in a matrix, pixel units 101b each having a fingerprint memory 103 and register 105 connected to each other are used, as shown in FIG. 14. As described above, the user's registered fingerprint data used for verification is stored in the fingerprint memory 103 in advance. When the fingerprint memory 103 is connected to the register 105, fingerprint data read by a fingerprint sensor circuit 102 can be easily stored as new registered fingerprint data.

Figure 15:
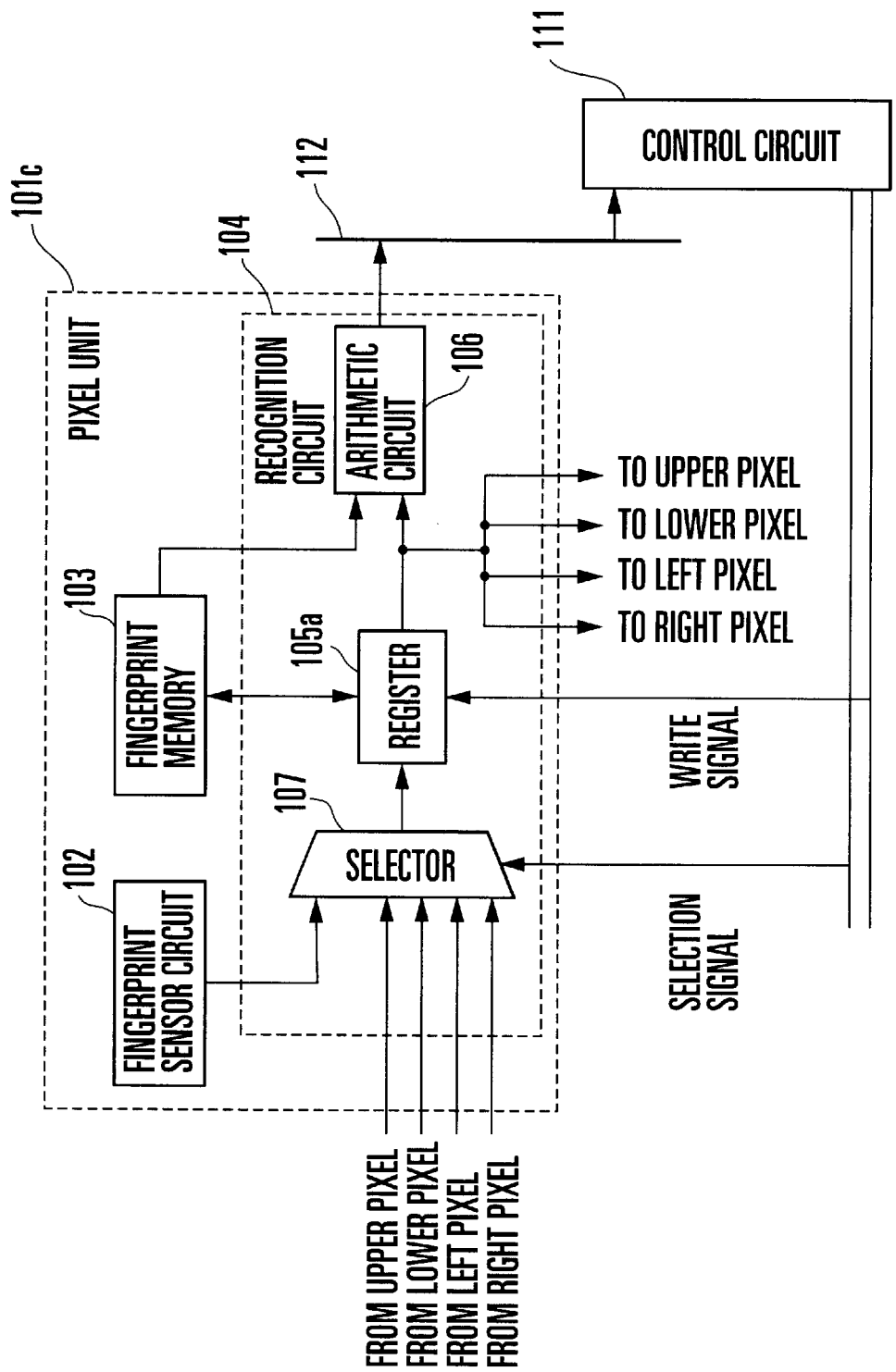
FIG. 15 is a view showing another arrangement of the pixel unit according to the fourth embodiment of the present invention.

Connection of the fingerprint memory and register can be applied to the fingerprint recognition apparatus shown in FIG. 10. In this case, a pixel unit 101c having the fingerprint memory 103 and register 105a connected to each other is used, as shown in FIG. 15. In a fingerprint recognition apparatus using the pixel unit 101c having a selector 107 shown in FIG. 15, when the data write line from a control circuit 111 is connected to one pixel unit in the pixel unit array, new registered fingerprint data from the control circuit 111 can be stored in the fingerprint memory. When the data write line from the control circuit 111 is connected to one pixel unit shown in FIG. 15, which is capable of shift, new registered fingerprint data can be sequentially written in all pixel units using this shift operation.

Fifth Embodiment

In the fingerprint recognition apparatus whose pixel unit array is shown in FIG. 12, to shift image data, a region of buffer units for holding data that stretch out due to the shift must be prepared around the pixel unit array. This buffer region increases the area of the fingerprint recognition apparatus. In the following embodiment, data omission in shift can be prevented without using the buffer units.

Figure 16:
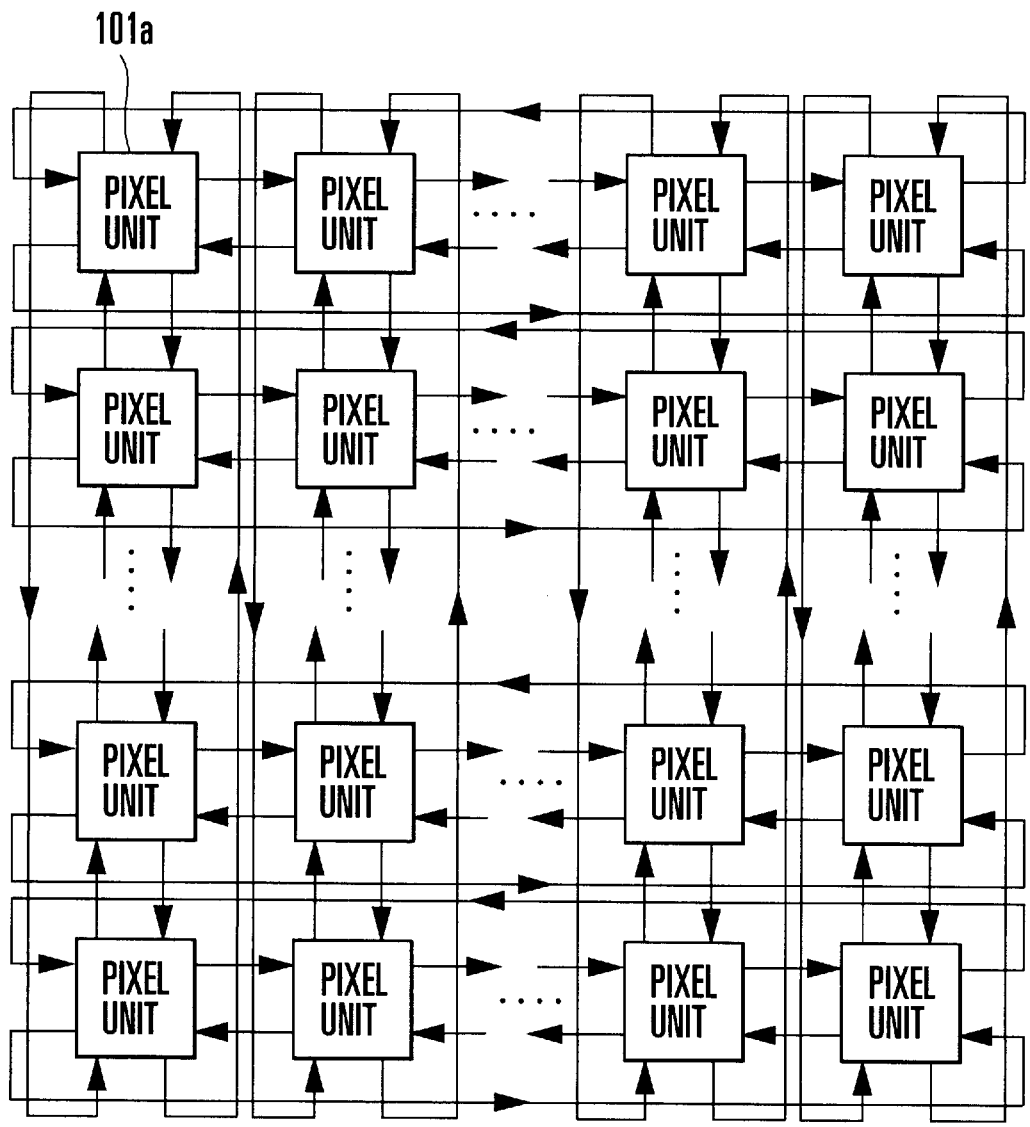
FIG. 16 is a plan view schematically showing the layout of pixel units according to the fifth embodiment of the present invention.

In the fingerprint recognition apparatus according to the fifth embodiment, a plurality of pixel units 101a are arrayed in a matrix to construct a pixel unit array, and each pixel unit 101a is connected to the upper, lower, left, and right pixel units 101a to shift image data, as shown in FIG. 16. In the fifth embodiment, each outermost pixel unit 101a of the pixel unit array is connected to a pixel unit 101a on the opposite side. For example, each pixel unit 101a of the leftmost column of the pixel unit array is connected to a corresponding pixel unit 101a of the rightmost column and the same row. Each pixel unit 101a of the uppermost row of the pixel unit array is connected to a corresponding pixel unit 101a of the lowermost row and the same column.

Figure 17:
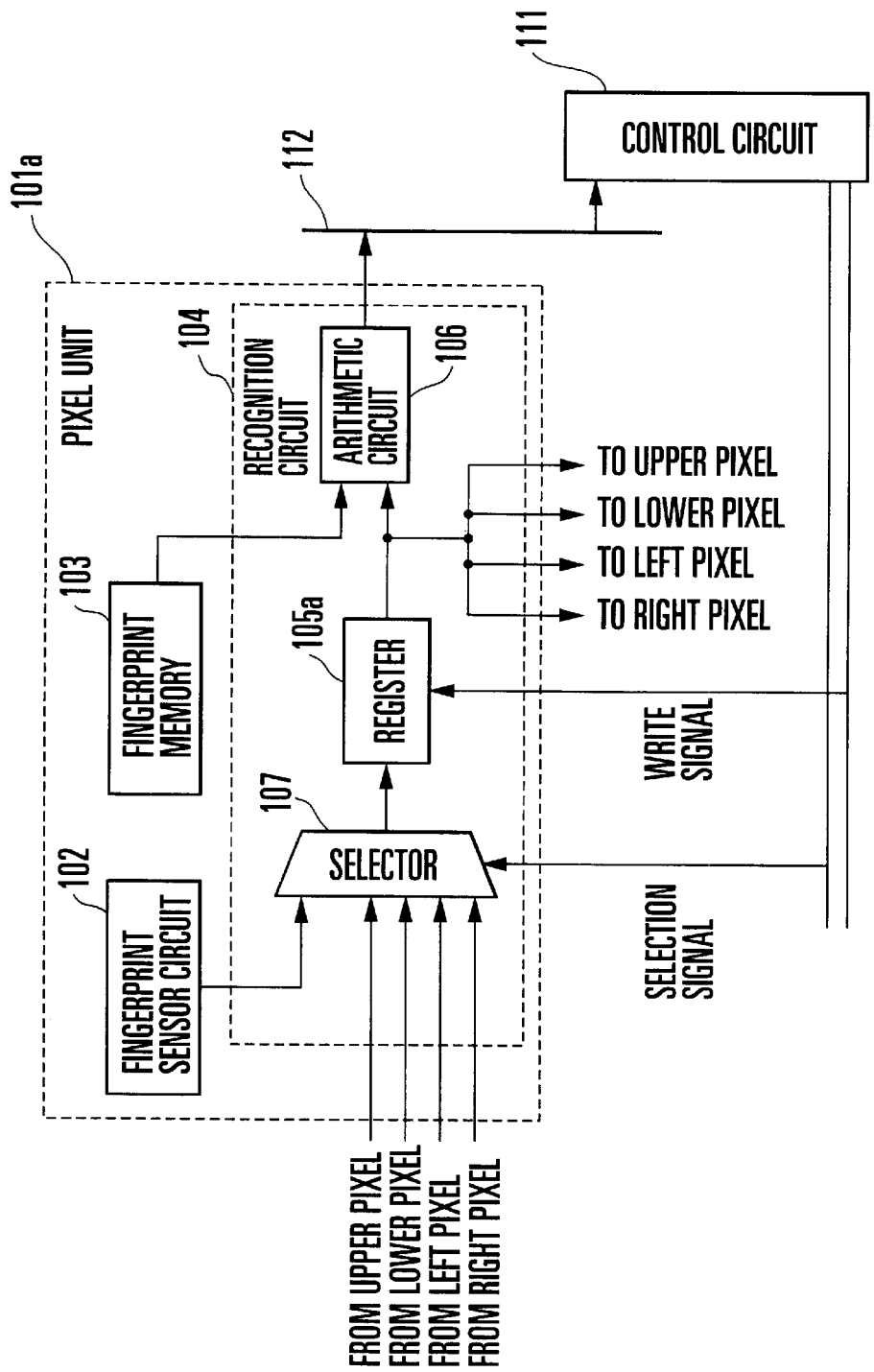
FIG. 17 is a view showing an arrangement of a pixel unit according to the fifth embodiment of the present invention.

The pixel unit 101a will be described again with reference to FIG. 17. This pixel unit has a fingerprint sensor circuit 102 for detecting a fingerprint pattern, which comprises a sensor element for converting the three-dimensional pattern of the skin surface of a finger (not shown) coming into contact with the element into an electrical signal and a sensor circuit for processing the electrical signal converted by the sensor element and outputting predetermined data, a fingerprint memory 103 holding the registered fingerprint of a user, and a recognition circuit 104 for collating the detected fingerprint data with the registered fingerprint data. The recognition circuit 104 comprises a register 105a for holding data output from the fingerprint sensor circuit 102 and transmitting this data to the selector of the upper, lower, left, or right pixel unit, and an arithmetic circuit 106 for performing logical calculation including collation between the output from the register 105a and the output from the fingerprint memory 103. The arithmetic circuits 106 of the respective pixel units 101a output the calculation results (recognition results) to a data bus 112.

Hence, the output from the register 105a of each outermost pixel unit 101a of the pixel unit array is connected to a selector 107 of a corresponding pixel unit 101a on the opposite side. For example, the register 105a of each pixel unit 101a of the leftmost column of the pixel unit array is connected to the selector of a corresponding pixel unit 101a of the rightmost column and the same row of the pixel unit array. The register 105a of each pixel unit 101a of the uppermost row of the pixel unit array is connected to the selector 107 of a corresponding pixel unit 101a of the lowermost row and the same column of the pixel unit array.

The recognition results from the respective pixel units 101a, which are output to the data bus 112, are totalized by a control circuit 111. The control circuit 111 also generates a write signal to the register 105a in the recognition circuit 104 and a selection signal (to be described later).

When a plurality of pixel units 101a having the above structure are arrayed to form a pixel unit array and connected to the control circuit 111 through the data bus 112, a fingerprint recognition apparatus which performs both detection and recognition of a fingerprint is realized.

The selector (selection means) 107 is inserted between the output of the fingerprint sensor circuit 102 and the input of the register 105a. Signals from the upper, lower, left, and right pixel units 101a are also input to the selector 107, and one of them is selected by the selection signal from the control circuit 111 and written in the register 105a. The register 105a transmits held data to the selectors 107 of the upper, lower, left, and right pixel units 101a.

When the pixel units 101a are arrayed in a matrix to construct the pixel unit array, as shown in FIG. 16, and the control signal is transmitted from the control circuit 111 to control the selector 107 of each pixel unit 101a, detected fingerprint data can be shifted in the vertical or horizontal direction.

Figures 18A, 18B:
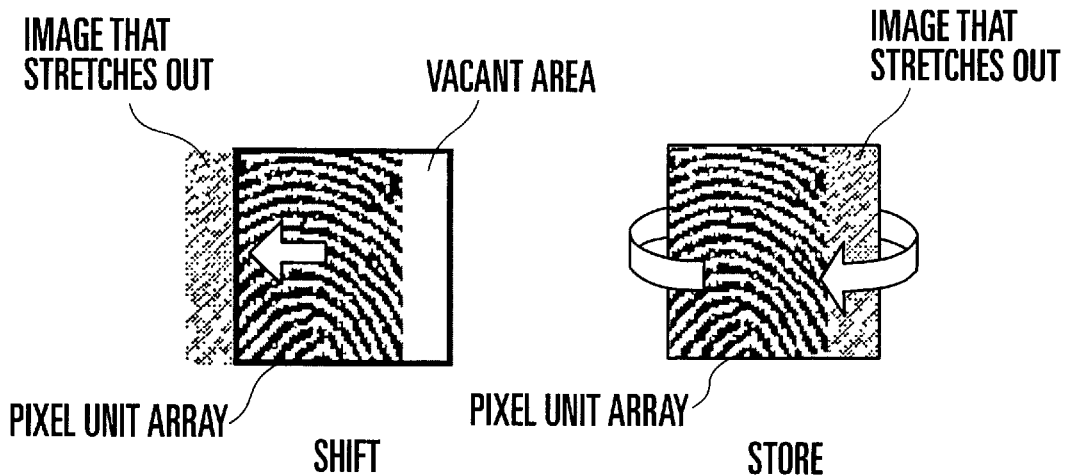
FIGS. 18A and 18B are plan views for explaining shift in the fifth embodiment of the present invention.

According to the fingerprint recognition apparatus with the above arrangement, image data stretch out from the pixel unit array due to the shift operation, and a number of pixel units on the opposite side of the image data that stretch out, which correspond to the number of image data that stretch out, become vacant, as shown in FIG. 18A. Next, the fingerprint recognition apparatus transfers the image data that stretch out due to the shift to the vacant pixel unit positions on the opposite side and stores the data in the pixel units by the storage operation, as shown in FIG. 18B. According to the fifth embodiment, since no buffers need be prepared around the pixel unit array to perform the shift operation, the area of the fingerprint recognition apparatus need not be increased.

Figure 19:
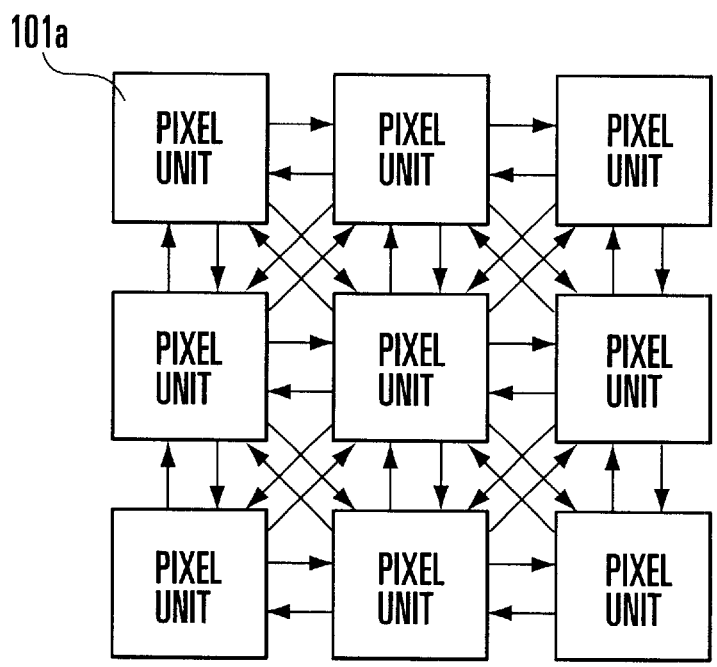
FIG. 19 is a plan view schematically showing the layout of pixel units according to the fifth embodiment of the present invention.

As shown in FIG. 19, when the pixel units of the pixel unit array are connected in the vertical and horizontal directions and also obliquely, the read image can be shifted in an arbitrary direction.

Sixth Embodiment

The sixth embodiment of the present invention will be described next.

Figure 20:
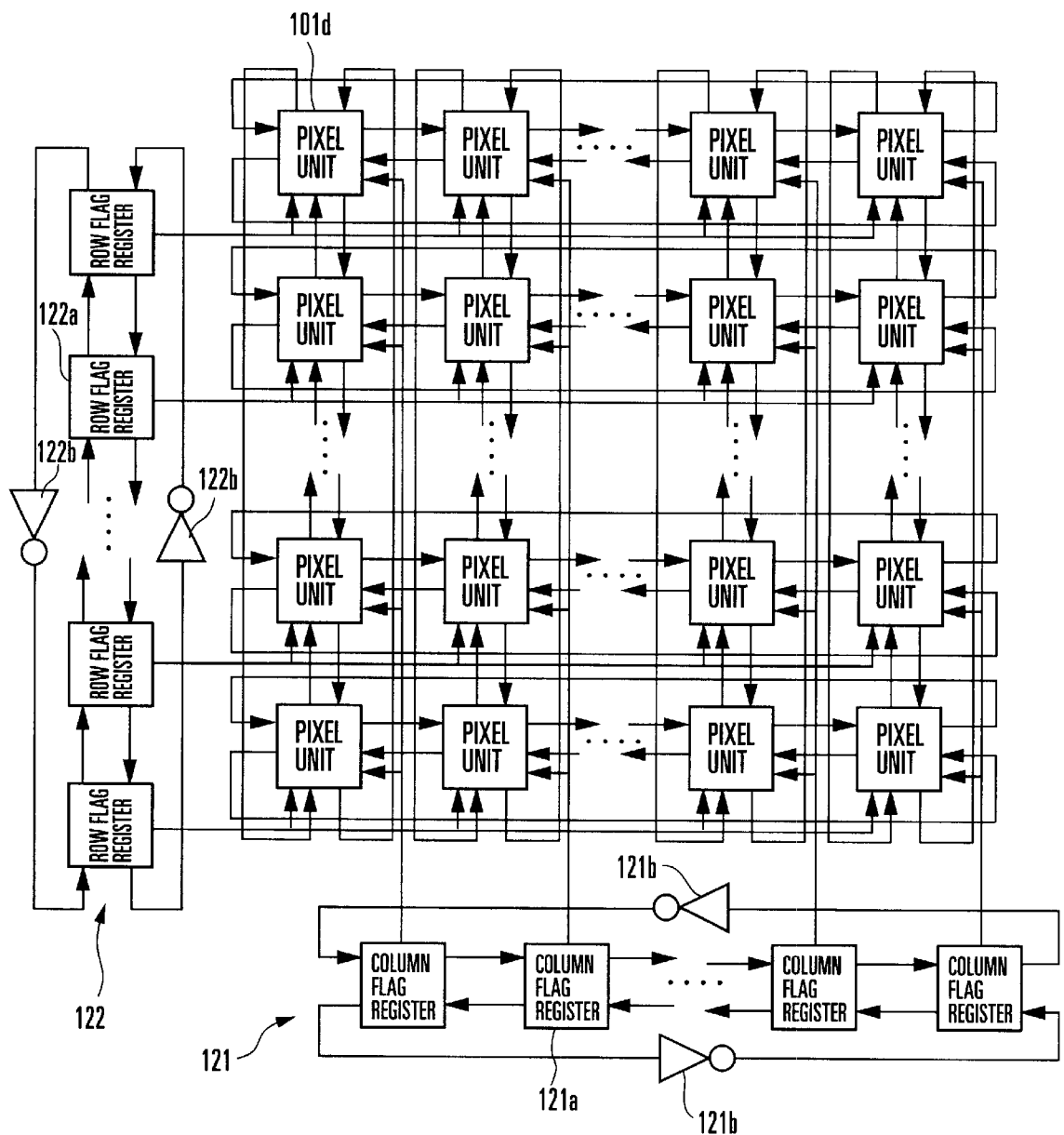
FIG. 20 is a plan view schematically showing the layout of pixel units and flag registers according to the sixth embodiment of the present invention.

In the fingerprint recognition apparatus of the sixth embodiment, a pixel unit array is constructed by pixel units 101d, and a column flag register array 121 and row flag register array 122 are arranged on sides of the pixel unit array, as shown in FIG. 20. The column flag register array 121 has column flag registers 121a arrayed in a line, and the row flag register array 122 has row flag register 122a arrayed in a line. Each column flag register 121a or row flag register 122a is connected to adjacent flag registers.

The column flag register 121a at one end of the column flag register array 121 is connected to the column flag register 121a at the other end through inverter elements 121b. The row flag register 122a at one end of the row flag register array 122 is connected to the row flag register 122a at the other end through inverter elements 122b.

The column flag register array 121 is arranged on the lower side of the pixel unit array of the pixel units 101d, and the output from each column flag register 121a is input to the pixel units 101d of the corresponding column of the pixel unit array. The row flag register array 122 is arranged on the left side of the pixel unit array, and the output from each row flag register 122a is input to the pixel units 101d of the corresponding row of the pixel unit array. The column flag register array 121 may be arranged on the upper side of the pixel unit array, and the row flag register array 122 may be arranged on the right side of the pixel unit array.

Figure 21:
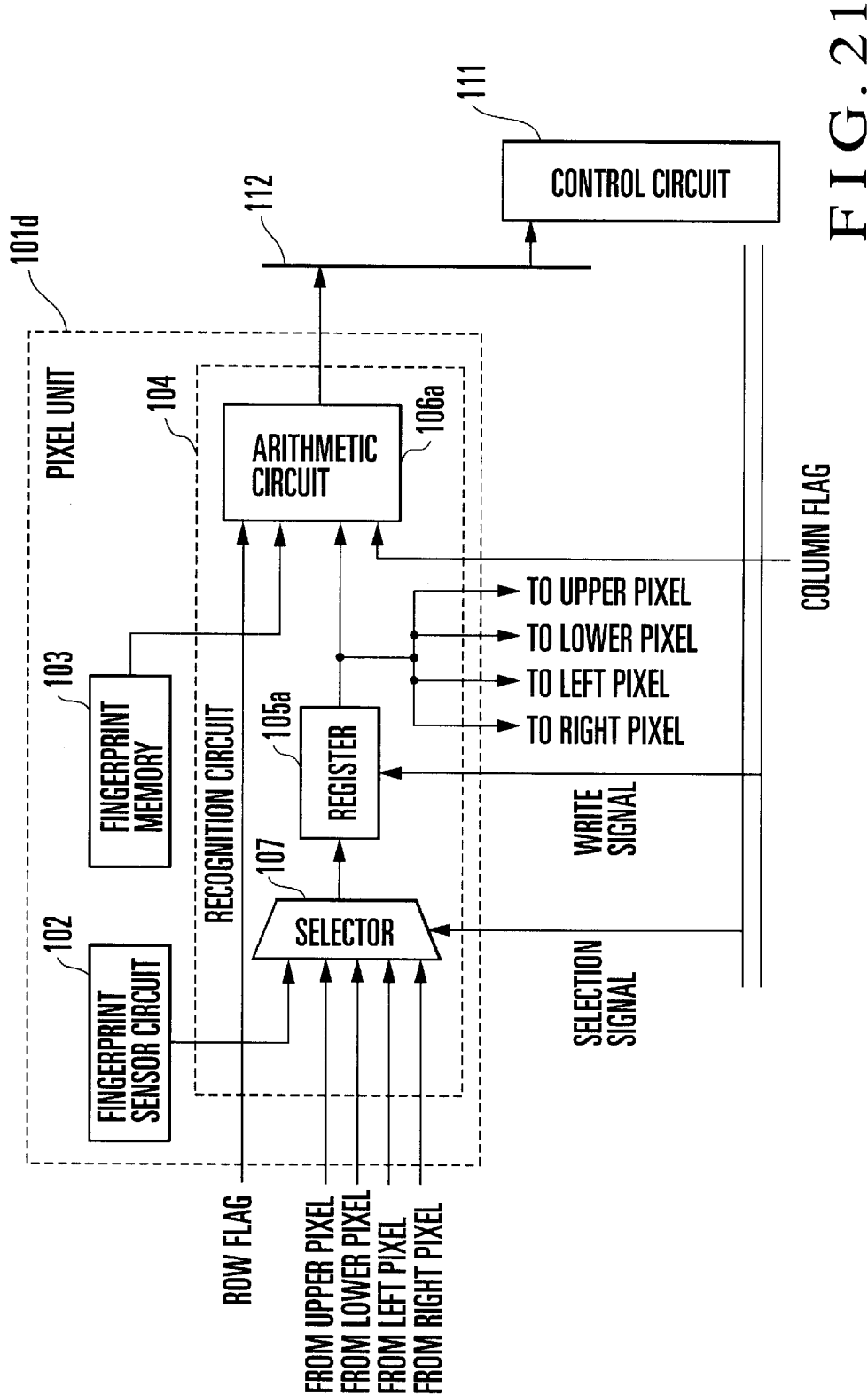
FIG. 21 is a view showing the arrangement of a pixel unit according to the sixth embodiment of the present invention.

The fingerprint recognition apparatus shown in FIG. 20 will be described in more detail with reference to FIG. 21. Circuits associated with the pixel unit 101d of the sixth embodiment are the same as those of the pixel unit 101a shown in FIG. 10 or 17 except that the signal (column flag) from a column flag register and the signal (row flag) from a row flag register are input to an arithmetic circuit 106a, and the arithmetic circuit 106a has four inputs.

Figure 22:
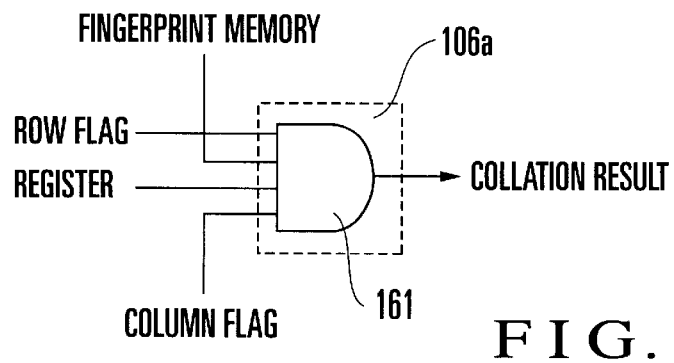
FIG. 22 is a view showing a partial structure of the pixel unit according to the sixth embodiment of the present invention.

FIG. 22 shows an example of the arithmetic circuit 106a. The arithmetic circuit 106a is formed from a 4-input AND circuit 161 which outputs "true" as a collation result when all of the signal from the row flag register, signal from the column flag register, signal from the fingerprint memory, and signal from the register are true.

Figure 23:
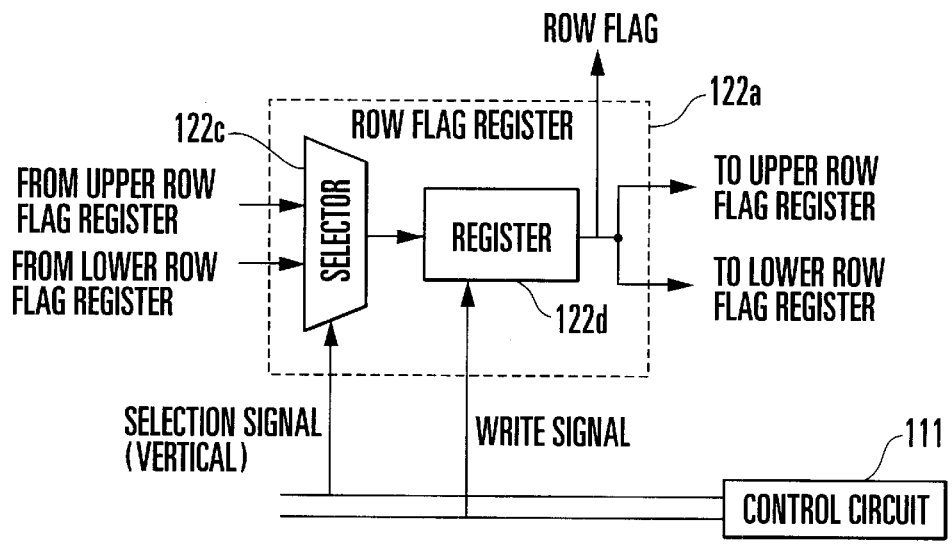
FIG. 23 is a view showing a partial structure of a flag register according to the sixth embodiment of the present invention.
Figure 24:
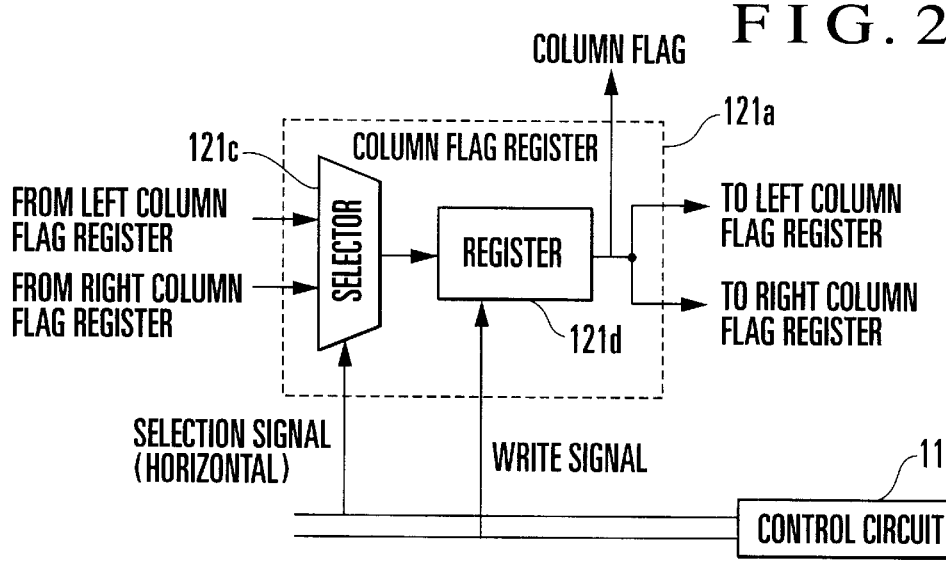
FIG. 24 is a view showing a partial structure of a flag register according to the sixth embodiment of the present invention.

FIG. 23 shows an example of the row flag register 122a. FIG. 24 shows an example of the column flag register 121a. As shown in FIG. 23, the row flag register 122a has a selector 122c and register 122d. The outputs from the upper and lower row flag registers 122a are input to the selector 122c. The register 122d outputs held data to the upper and lower row flag registers 122a. As shown in FIG. 24, the column flag register 121a has a selector 122c and register 122d.

The outputs from the left and right column flag registers 121a are input to the selector 121c. The register 121d outputs held data to the left and right column flag registers 121a.

A selection signal from a control circuit 111 to the selector 122c of the row flag register 122a and a write signal from the control circuit 111 to the register 122d are identical to the control signal output from the control circuit 111 to each pixel unit 101d. For this reason, when the pixel unit array shifts input images in the vertical direction, the row flag registers 122a of the row flag register array 122 (FIG. 20) also shift held data in the vertical direction. Since the row flag registers 122a at the two ends are connected through the inverter elements 122b, data sent to the row flag register 122a at the other end by shift is inverted.

Similarly, a selection signal from the control circuit 111 to the selector 121c of the column flag register 121a and a write signal from the control circuit 111 to the register 121d are identical to the control signal output from the control circuit 111 to each pixel unit 101d. For this reason, when the pixel unit array shifts input images in the horizontal direction, the column flag registers 121a of the column flag register array 121 (FIG. 20) also shift held data in the horizontal direction. Since the column flag registers 121a at the two ends are connected through the inverter elements 121b, data sent to the column flag register 121a at the other end by shift is inverted.

Figure 25A:
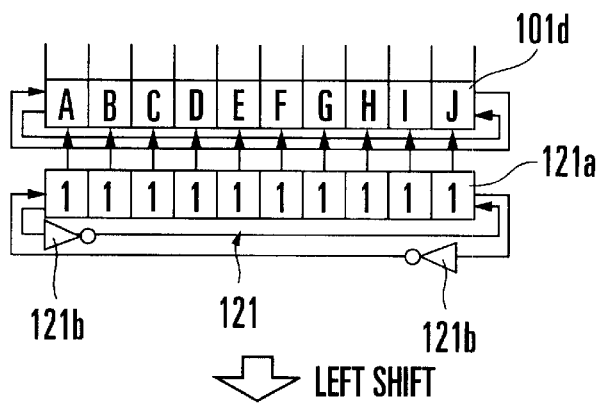
FIGS. 25A, 25B, 25C, and 25D are explanatory views for explaining shift in the sixth embodiment of the present invention.

As described above, in the sixth embodiment, since the column flag registers are provided in correspondence with the rows of the pixel unit array, respectively, the fingerprint recognition apparatus of the sixth embodiment operates as shown in FIGS. 25A to 25D. FIGS. 25A to 25D show the pixel units 101d of the lowermost row of the pixel unit array and the column flag register array 121 formed from the column flag registers 121a. As shown in FIG. 25A, the pixel units 101*d* of the lowermost row read image data "A", "B", "C", "D", "E", "F", "G", "H", "I", and "J" from the left, respectively, first. As shown in FIG. 25A, all the column flag registers 121*a* hold "1" in the initial state.

Figure 25B:
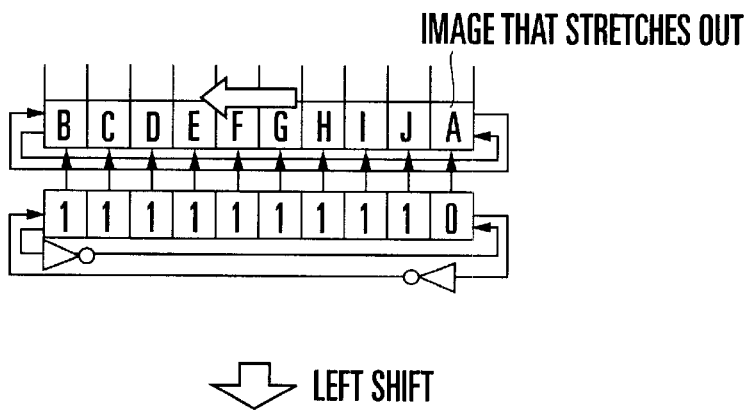

The images in the pixel unit array are shifted to the left by one pixel unit from the initial state shown in FIG. 25A. At this time, as shown in FIG. 25B, the data "A" held by the leftmost pixel unit 101*d* stretches out and is transferred to the rightmost pixel unit 101*d* on the opposite side and held. Simultaneously, the left shift signal is also sent to the column flag registers 121*a*, so the column flag register array 121 also perform left shift. In left shift in the column flag register array 121, data that stretches out from the leftmost column flag register 121*a* is transferred to the rightmost column flag register 121*a* and held while the polarity is inverted by the inverter element 121*b*.

Figure 25C:
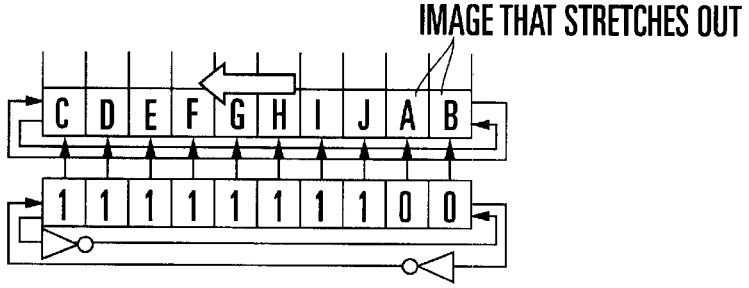
Figure 25D:
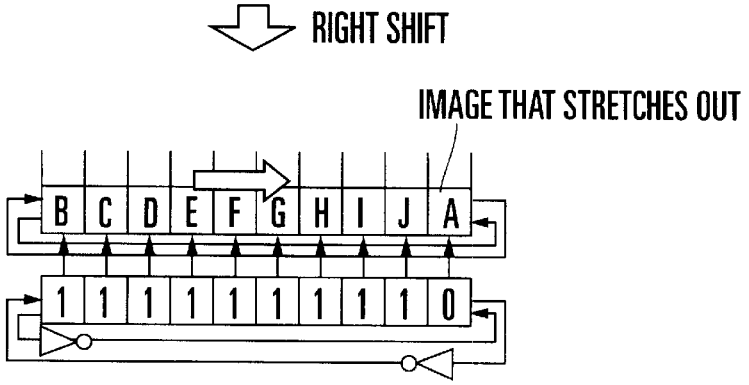

By further left shift, the second column flag register 121*a* from the right also outputs "0", as shown in FIG. 25C. Conversely, when the data are shifted to the right by one pixel unit from the state shown in FIG. 25B, data that stretches out returns to the original position, and data "0" that stretches out from the column flag register 121*a* at the right end is inverted to "1" through the inverter element 121b, transferred to the column flag register 121*a* at the left end, and held, as shown in FIG. 25D. Data "1" from the third column flag register 121*a* from the right is transferred and held by the second column flag register 121*a* from the right. In the column flag register array 121, only the column flag register 121*a* at the right end outputs "0".

As described above, data that stretches out from the column flag register 121*a* at the left end due to the left shift is inverted to "0" and held by the column flag register 121*a* on the opposite side. For this reason, it can be determined that a column where the output from the corresponding column flag register 121*a* is "0" is holding the data that stretches out.

Figures 26A, 26B, 26C:
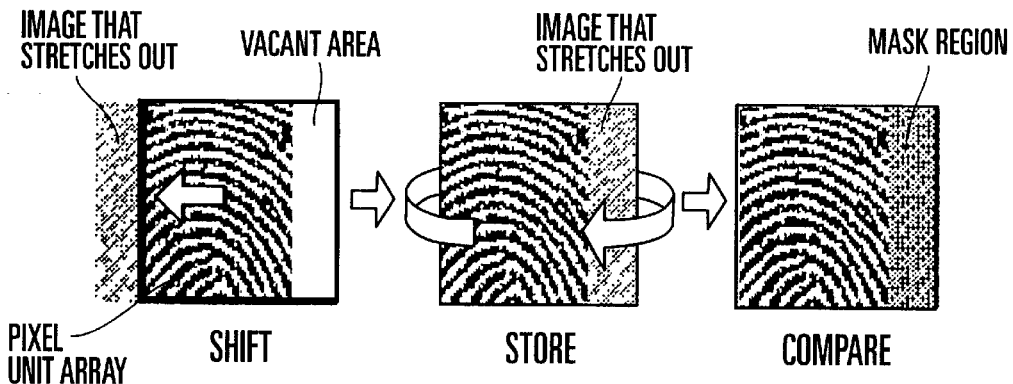
FIG. 26 is a plan view for explaining shift in the sixth embodiment of the present invention.

First, as shown in FIG. 26A, image data stretch out from the pixel unit array due to the shift operation, and a number of pixel units on the opposite side of the image data that stretch out, which correspond to the number of image data that stretch out, become vacant. Next, the fingerprint recognition apparatus transfers the image data that stretch out due to the shift to the vacant pixel unit positions on the opposite side and stores the data in the pixel units by the storage operation, as shown in FIG. 26B.

As for the column of pixel units holding the image data that stretch out, the column flag register connected to these pixel units outputs "0". For this reason, as shown in FIG. 26C, the column of pixel units for which the output from the column flag register is "0" can be defined as a mask region.

In the fingerprint recognition apparatus of the fifth embodiment, when shifted image data are to be 15 collated with user's registered data held in the fingerprint memory, data that stretch out must be, e.g., masked not to be collated. This is because the data that stretch out are held at positions different from the original positions.

In the sixth embodiment, as shown in FIG. 26C, since the column of pixel units for which the output from the column flag register is "0" can be set as a mark region, collation of the data that stretch out can be inhibited.

Figure 27:
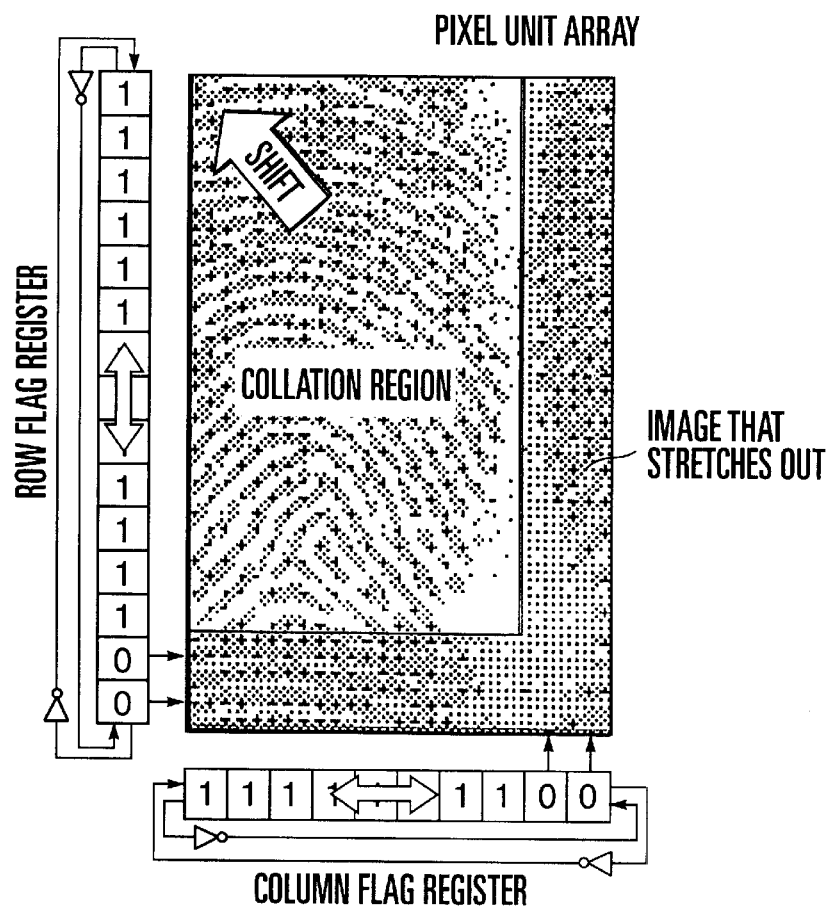
FIG. 27 is a plan view for explaining shift in the sixth embodiment of the present invention.

Masking in the column direction of the pixel unit array by the column flag register array has been described above. This also applies to masking in the row direction of the pixel unit array by the row flag register array. FIG. 27 shows the actual image of the actual pixel unit array using the column flag registers and row flag registers. FIG. 27 shows a state wherein shift is performed twice to the left and twice to the upper side, and images that stretch out are held at pixel unit positions on the opposite sides. As shown in FIG. 27, according to the sixth embodiment, column and row flag registers corresponding to portions where data that stretch out are held output "0" to mask the portions in collation.

In the above description of the sixth embodiment, one column or row flag register is made to correspond to one column or row of the pixel unit array. For example, when many data are to be simultaneously shifted, one column or row flag register can be made to correspond to a plurality of columns or rows of pixel units. In the above sixth embodiment, the column flag register array and row flag register array are used. However, only the column flag register array may be used, or only the row flag register array may be used.

Seventh Embodiment

The seventh embodiment of the present invention will be described next.

Figure 28:
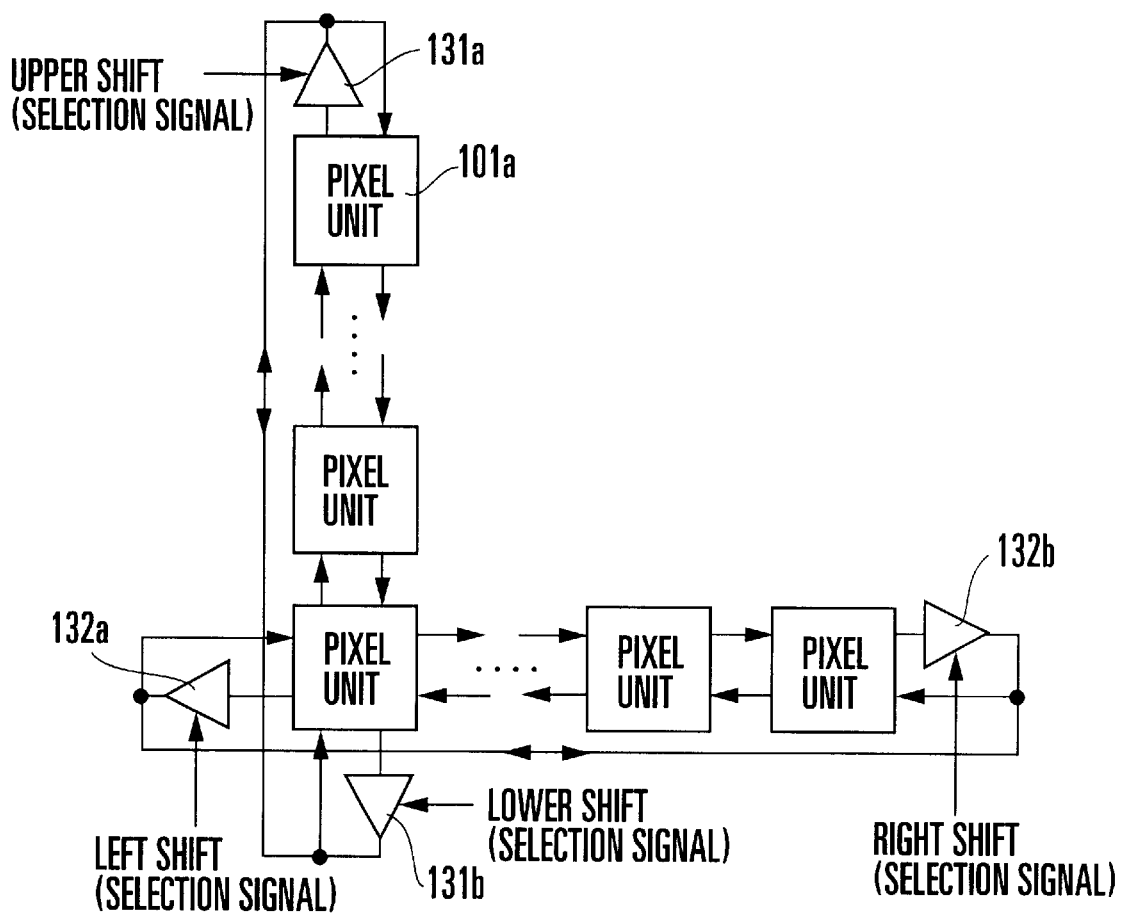
FIG. 28 is a plan view schematically showing the layout of pixel units according to the seventh embodiment of the present invention.

In the seventh embodiment, 3-state buffers 131*a*, 131*b*, 132*a*, and 132*b* are used to connect pixel units at the ends of a pixel unit array, as shown in FIG. 28. The output signal upward from an uppermost pixel unit 101*a* of the pixel unit array is connected to the input of the 3-state buffer 131*a*. The output from the 3-state buffer 131*a* is connected from the lower side to the input of the lowermost pixel unit 101*a* of the pixel unit array. Similarly, the lowermost pixel unit 101*a* of the pixel unit array is connected to the uppermost pixel unit 101*a* of the pixel unit array through the 3-state buffer 131*b* which is connected to the signal line used to connect the uppermost pixel unit 101*a* of the pixel unit array to the lowermost pixel unit 101*a* of the pixel unit array.

The output signal to the left from a leftmost pixel unit 101*a* of the pixel unit array is connected to the input of the 3-state buffer 132*a*. The output from the 3-state buffer 132*a* is connected from the right side to the input of the rightmost pixel unit 101*a* of the pixel unit array. Similarly, the rightmost pixel unit 101*a* of the pixel unit array is connected to the leftmost pixel unit 101*a* of the pixel unit array through the 3-state buffer 132*b* which is connected to the signal line used to connect the leftmost pixel unit 101*a* of the pixel unit array to the rightmost pixel unit 101*a* of the pixel unit array.

Figure 29:
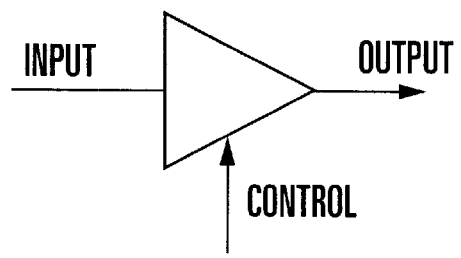
FIG. 29 is a view showing the structure of a 3-state buffer according to the seventh embodiment of the present invention.

Each 3-state buffer has an input terminal, output terminal, and control terminal, as shown in FIG. 29. When the control signal (selection signal) to the control terminal is "true", data input to the input terminal is output to the output terminal. To the contrary, when the control signal to the control terminal is "false", the output terminal is set in a high-impedance state.

Of shift signals transmitted from a control circuit (not shown) to each pixel unit 101*a*, a selection signal representing upward shift is input to the control terminal of the 3-state buffer 131*a*, a selection signal representing downward shift is input to the control terminal of the 3-state buffer 131*b*, a selection signal representing left shift is input to the control terminal of the 3-state buffer 132*a*, and a selection signal representing right shift is input to the control terminal of the 3-state buffer 132*b*.

As described above, in the seventh embodiment, since the pixel units at two ends of the pixel unit array are connected to one signal line by bus connection using 3-state buffers, for example, the signal line used for the left shift operation and that used for the right shift operation can share one signal line. Since signal lines used for shifts in the reverse directions can share one signal line, the fingerprint recognition apparatus of the seventh embodiment can halve the number of signal lines passing through the pixel unit array in the vertical direction. Simultaneously, the number of signal lines passing through the pixel unit array in the horizontal direction can also be halved.

Eighth Embodiment

The eighth embodiment of the present invention will be described next.

Figure 30:
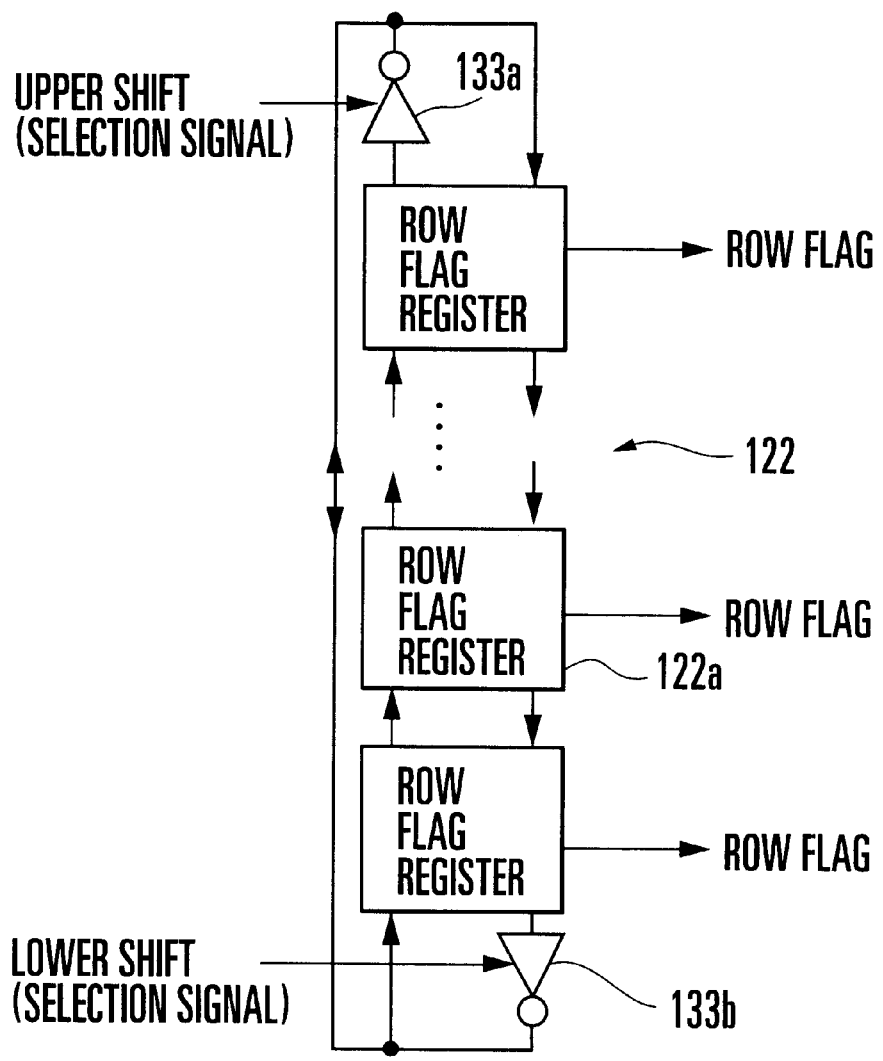
FIG. 30 is a plan view showing a layout of flag registers according to the eighth embodiment of the present invention.

In the eighth embodiment, 3-state inverters are used to connect flag registers at the two ends of each flag register array shown in the sixth embodiment. This will be described in association with the row flag register array. As shown in FIG. 30, the output signal upward from an uppermost row flag register 122a of a row flag register array 122 is connected to the input of a 3-state inverter 133a. The output from the 3-state inverter 133a is connected from the lower side to the input of the lowermost row flag register 122a.

The output signal downward from the lowermost row flag register 122a of the row flag register array 122 is connected to the input of a 3-state inverter 133b. The output from the 3-state inverter 133b is connected from the upper side to the input of the uppermost row flag register 122a.

The lowermost row flag register 122a is connected to the uppermost row flag register 122a through the 3-state inverter 133b which is connected to the signal line used to connect the uppermost row flag register 122a to the lowermost row flag register 122a. That is, connection from the uppermost row flag register to the lowermost row flag register and that from the lowermost row flag register to the uppermost row flag register share one signal line.

Figure 31:
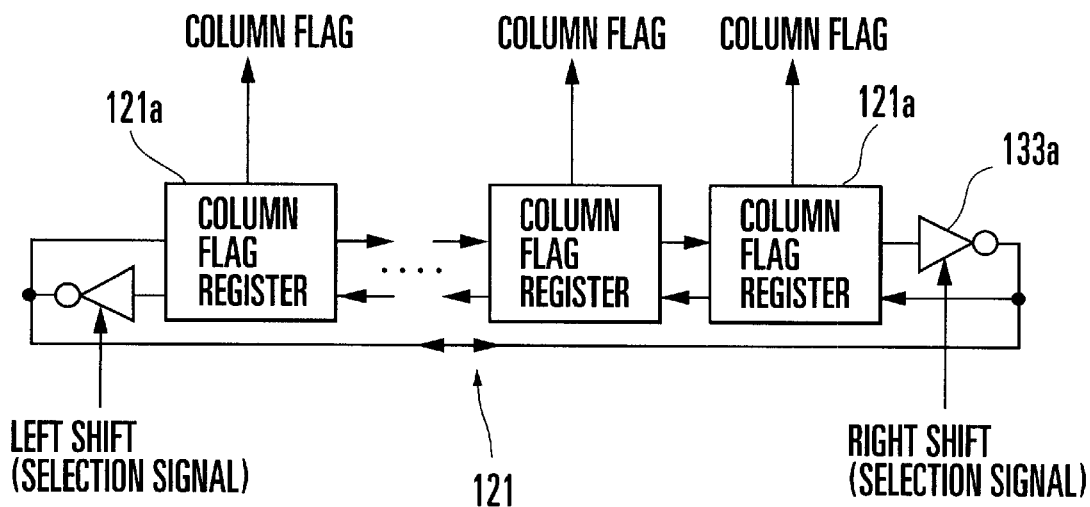
FIG. 31 is a plan view showing another layout of flag registers according to the eighth embodiment of the present invention.

This also applies to the column flag register array. As shown in FIG. 31, the output signal to the left from a leftmost column flag register 121a of a column flag register array 121 is connected to the input of a 3-state inverter 134a. The output from the 3-state inverter 134a is connected from the right to the input of the rightmost column flag register 121a.

The output signal to the right from the rightmost column flag register 121a of the column flag register array 121 is connected to the input of a 3-state inverter 134b. The output from the 3-state inverter 134b is connected from the left to the input of the leftmost column flag register 121a.

The rightmost column flag register 121a is connected to the leftmost column flag register 121a through the 3-state inverter 134b which is connected to the signal line used to connect the leftmost column flag register 121a to the rightmost column flag register 121a. That is, connection from the leftmost column flag register to the rightmost column flag register and that from the rightmost column flag register to the leftmost column flag register share one signal line.

Figure 32:
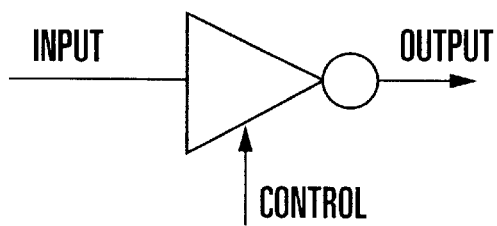
FIG. 32 is a view showing the structure of a 3-state inverter according to the eighth embodiment of the present invention.
Figure 33:
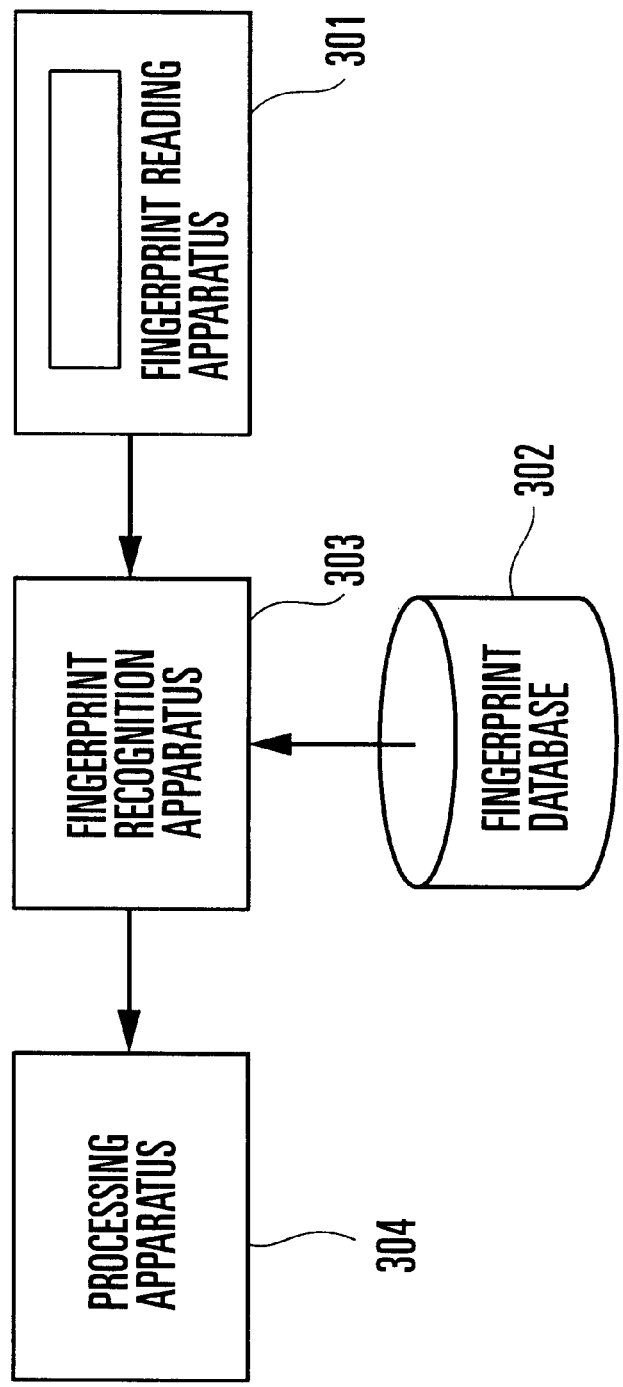
FIG. 33 is a block diagram showing the arrangement of a conventional fingerprint recognition system.

Each 3-state inverter has an input terminal, output terminal, and control terminal, as shown in FIG. 32. When the control signal to the control terminal is "true", data input to the input terminal is inverted in its polarity and output to the output terminal. When the control signal to the control terminal is "false", the output terminal is set in a high-impedance state.

As described above, in the eighth embodiment, since the flag registers at two ends of each flag register array in the above-described sixth embodiment are connected to one signal line by bus connection using 3-state inverters, for example, the signal line used for the left shift operation and that used for the right shift operation can share one signal line. Since signal lines used for shifts in the reverse directions can share one signal line, the fingerprint recognition apparatus of the eighth embodiment can use only one signal line passing through each flag register array.

As has been described above, the fingerprint recognition apparatus according to the present invention has a plurality of pixel units each comprising a sensor element for converting the three-dimensional pattern of the skin surface of a finger coming into contact with the element into an electrical signal, a sensor circuit for processing the electrical signal converted by the sensor element and outputting predetermined data, a fingerprint memory in which fingerprint data representing the three-dimensional pattern of the skin surface is registered in advance, and an arithmetic circuit for collating data sent from the sensor circuit with the fingerprint data in the fingerprint memory and outputting the collation result.

According to the present invention having this arrangement, both reading and recognition of a fingerprint at the pixel unit portion can be performed in one pixel unit. When a plurality of pixel units are formed on one semiconductor integrated circuit, system components for fingerprint recognition can be constructed on one semiconductor chip. As a consequence, according to the present invention, the system for fingerprint recognition can be applied to a compact device such as an IC card or portable device at low cost.

What is claimed is:

1. A fingerprint recognition apparatus comprising:
   a plurality of pixel units each having:
      a sensor element for converting a three-dimensional pattern of a skin surface of a finger coming into contact with said sensor element into an electrical signal;
      a sensor circuit for processing the electrical signal converted by said sensor element and outputting predetermined data;
      a fingerprint memory in which fingerprint data representing the three-dimensional pattern of the skin surface of the finger is registered in advance; and
      an arithmetic circuit for collating the data output from said sensor circuit with the fingerprint data in said fingerprint memory and outputting a collation result, wherein said plurality of pixel units are arrayed in a matrix.

2. An apparatus according to claim 1, further comprising a control circuit for totalizing collation results output from said arithmetic circuit.

3. An apparatus according to claim 2, wherein
   said control circuit generates a fingerprint recognition result on the basis of totalized calculation results of said pixel units.

4. An apparatus according to claim 1, wherein
   said apparatus further comprises holding means for holding the data output from said sensor circuit, and
   the data held by said holding means is processed by said arithmetic circuit.

5. An apparatus according to claim 1, wherein
   said apparatus further comprises
      selection means, arranged in units of pixel units, for receiving the data from said sensor circuit in the same pixel unit and data from peripheral pixel units and selectively outputting predetermined data, and
      holding/transfer means, arranged in units of pixel units, for holding the data output from said selection means and outputting the data to said arithmetic circuit and selection means in said peripheral pixel units, and
      said control circuit outputs a selection signal for causing said selection means to select the predetermined data and a write signal for causing said holding/tansfer means to output the held data to said arithmetic circuit and said selection means in said peripheral pixel units.

6. An apparatus according to claim 5, further comprising a buffer unit arranged around said pixel units arrayed in the matrix to hold data output from an outermost pixel unit.

7. An apparatus according to claim 6, wherein
said buffer unit comprises
   selection means for receiving the data from said outermost pixel unit and data output from peripheral buffer units and selectively outputting predetermined data, and
   holding/transfer means for holding the data output from said selection means and outputting the data to said outermost pixel unit and said peripheral buffer units.

8. An apparatus according to claim 5, wherein
an output to an upper pixel unit from holding/transfer means in an uppermost pixel unit of said plurality of pixel units arrayed in the matrix is connected to selection means in a lowermost pixel unit of the same column,
an output to a lower pixel unit from holding/transfer means in said lowermost pixel unit of said plurality of pixel units arrayed in the matrix is connected to selection means in said uppermost pixel unit of the same column,
an output to a left pixel unit from holding/transfer means in a leftmost pixel unit of said plurality of pixel units arrayed in the matrix is connected to selection means in a rightmost pixel unit of the same row, and
an output to a right pixel unit from holding/transfer means in said rightmost pixel unit of said plurality of pixel units arrayed in the matrix is connected to selection means in said leftmost pixel unit of the same row.

9. An apparatus according to claim 8, wherein
said apparatus further comprises a plurality of flag registers arranged in units of rows or columns of said plurality of pixel units arrayed in the matrix, and a register arranged in said flag register holds one of first and second data, said flag registers controlling to output collation results from arithmetic circuits in pixel units of the same rows or column when said register holds the first data,
said flag register comprises a selector for receiving outputs from registers of two adjacent flag registers, selecting one of the outputs in accordance with the selection signal from said control circuit, and outputting the selected output to said register,
said register outputs one of the held first and second data to a selector in an adjacent flag register in accordance with the write signal from said control circuit, and
an output from a register in a flag register at one end of an array of said plurality of flag registers is input to a selector in a flag register at the other end through an inverter element.

10. An apparatus according to claim 9, wherein said flag register is arranged in units of rows and columns of said plurality of pixel units arrayed in the matrix.

11. An apparatus according to claim 8, wherein
said apparatus further comprises
   first and second 3-state buffers each for outputting, from an output terminal, a signal input from an input terminal in accordance with the selection signal from said control circuit, and
   a connection line connected to an output of holding/transfer means and an input of selection means of a pixel unit at one end in said plurality of pixel units arrayed in the matrix, and an output of holding/transfer means and an input of selection means of a pixel unit at the other end,
   the output of said holding/transfer means in said pixel unit at said one end is connected to said input terminal of said first 3-state buffer and further connected from said output terminal of said first 3-state buffer to said selection means in said pixel unit at said other end through said connection line, and
   the output of said holding/transfer means in said pixel unit at said other end is connected to said input terminal of said second 3-state buffer and further connected from said output terminal of said first 3-state buffer to said selection means in said pixel unit at said one end through said connection line.

12. An apparatus according to claim 9, wherein
said apparatus further comprises
   first and second 3-state inverters each for inverting a signal input from an input terminal and outputting the inverted signal from an output terminal in accordance with the selection signal from said control circuit, and
   a transfer line connected to an output of a register and an input of a selector of a flag register at one end of said array of said plurality of flag registers, and an output of a register and an input of a selector of a flag register at the other end,
   the output of said register in said flag register at said one end is connected to said input terminal of said first 3-state inverter and further connected from said output terminal of said first 3-state inverter to said selector in said flag register at said other end through said transfer line, and
   the output of said register in said flag register at said other end is connected to said input terminal of said second 3-state inverter and further connected from said output terminal of said first 3-state inverter to said selector in said flag register at said one end through said transfer line.

13. An apparatus according to claim 4, wherein
said holding means and said fingerprint memory of said pixel unit are connected, and data is written in said fingerprint memory through said holding means.

14. An apparatus according to claim 1, wherein
said sensor element has a contact electrode having a contact surface externally exposed and detects an electrostatic capacitance generated on said contact electrode.

15. An apparatus according to claim 1, wherein
said sensor element has an upper electrode, and a lower electrode separated from said upper electrode by a predetermined distance to oppose said upper electrode, and detects a change in capacitance between said upper electrode and said lower electrode.

16. An apparatus according to claim 15, wherein
a cushioning material is inserted between said upper electrode and said lower electrode.

17. An apparatus according to claim 15, wherein
a space is formed between said upper electrode and said lower electrode.

18. An apparatus according to claim 8, wherein
when the data held by said holding/transfer means in said pixel unit is transmitted to said selection means of said peripheral pixel units of said pixel unit, data held by said holding/transfer means are shifted in said plurality of pixel units arrayed in the matrix in an opposite direction of pixel units selected by said selection means of said plurality of pixel units arrayed in the matrix.

19. An apparatus according to claim 9, wherein
when the second data are held by said registers in said flag registers, the second data held by said registers is output to a selector in an adjacent flag register in accordance with the write signal from said control circuit, and when an output from said register in said flag register at one end of said array of said plurality of flag registers is input to said selector in said flag register at the other end through said inverter element, the first data is held by said register in said flag register at said other end, so that data held by pixel units of a row or a column of said plurality of pixel units arrayed in the matrix are not collated by said arithmetic circuit, the row or the column corresponding to said flag register at said other end.

20. An apparatus according to claim 11, wherein
in accordance with the selection signal from said control circuit, an output from said holding/transfer means in said pixel unit at said one end is input to said selection means in said pixel unit at said other end through said input terminal of said first 3-state buffer, said output terminal and said connection line, and the data held by said holding/transfer means in said pixel unit at said one end is transferred to said selection means in said pixel unit at said other end.

21. An apparatus according to claim 12, wherein
in accordance with the selection signal from said control circuit, an output from said register in said flag register at said one end is input to said selector in said flag register at said other end through said input terminal of said first 3-state inverter, said output terminal and said transfer line, and the first or second data held by said register in said flag register at said one end is inverted and transferred to said selector in said flag register at said other end.

22. A data processing method comprising the steps of:
arranging a plurality of pixel units arrayed in a matrix, each of said pixel units having a sensor element for converting a three-dimensional pattern of a skin surface of a finger coming into contact with said sensor element into an electrical signal, a sensor circuit for processing the electrical signal converted by said sensor element and outputting predetermined data, a fingerprint memory in which fingerprint data representing the three-dimensional pattern of the skin surface of the finger is registered in advance, and an arithmetic circuit for collating the data output from said sensor circuit with the fingerprint data in said fingerprint memory and outputting a collation result;
arranging selection means, in units of pixel units, for receiving the data from said sensor circuit in the same pixel unit and data from peripheral pixel units and selectively outputting predetermined data;
arranging holding/transfer means, in units of pixel units, for holding the data output from said selection means and outputting the data to said arithmetic circuit and selection means in said peripheral pixel units;
connecting an output to an upper pixel unit from holding/transfer means in an uppermost pixel unit of said plurality of pixel units arrayed in the matrix to selection means in a lowermost pixel unit of the same column, connecting an output to a lower pixel unit from holding/transfer means in said lowermost pixel unit of said plurality of pixel units arrayed in the matrix to selection means in said uppermost pixel unit of the same column connected an output to a left pixel unit from holding/transfer means in a leftmost pixel unit of said plurality of pixel units arrayed in the matrix to selection means in a rightmost pixel unit of the same row, and connecting an output to a right pixel unit from holding/transfer means in said rightmost pixel unit of said plurality of pixel units arrayed in the matrix to selection means in said leftmost pixel unit of the same row; and when the data held by said holding/transfer means in said pixel unit is transmitted to said selection means of said peripheral pixel units of said pixel unit, shifting data held by said holding/transfer means in said plurality of pixel units arrayed in the matrix in an opposite direction of pixel units selected by said selection means of said plurality of pixel units arrayed in the matrix.

23. A method according to claim 22, further comprising the steps of:
arranging a plurality of flag registers arranged in units of rows or columns of said plurality of pixel units arrayed in the matrix, and a register arranged in said flag register holds one of first and second data, when said register holds the first data, controlling to output collation results from arithmetic circuits in pixel units of the same rows or columns;
causing said flag register to comprise a selector for receiving outputs from registers of two adjacent flag registers, selecting one of the outputs in accordance with the selection signal from said control circuit, and outputting the selected output to said register;
causing said register in said flag register to hold the second data;
outputting the second data held by said registers to a selector in an adjacent flag register in accordance with the write signal from said control circuit, and inputting an output from said register in said flag register at one end of said array of said plurality of flag registers to said selector in said flag register at the other end through said inverter element to cause said register in said flag register at said other end to hold the first data; and
excluding data held by pixel units of a row or a column of said plurality of pixel units arrayed in the matrix from collation by said arithmetic circuit, the row or the column corresponding to said flag register at said other end.

24. A method according to claim 22, further comprising the steps of:
arranging first and second 3-state buffers each for outputting, from an output terminal, a signal input from an input terminal in accordance with the selection signal from said control circuit;
arranging a connection line connected to an output of holding/transfer means and an input of selection means of a pixel unit at one end in said plurality of pixel units arrayed in the matrix, and an output of holding/transfer means and an input of selection means of a pixel unit at the other end;
connecting the output of said holding/transfer means in said pixel unit at said one end to said input terminal of said first 3-state buffer and further connecting the output from said output terminal to said selection means in said pixel unit at said other end through said connection line;
connecting the output of said holding/transfer means in said pixel unit at said other end to said input terminal of said second 3-state buffer and further connecting the output from said output terminal to said selection means in said pixel unit at said one end through said connection line; and in accordance with the selection signal from said control circuit, inputting an output from said holding/transfer means in said pixel unit at said one end to said selection means in said pixel unit at said other end through said input terminal of said first 3-state buffer, said output terminal and said connection line, and transferring the data held by said holding/transfer means in said pixel unit at said one end to said selection means in said pixel unit at said other end.

25. A method according to claim 23, further comprising the steps of:

arranging first and second 3-state inverters each for inverting a signal input from an input terminal and outputting the inverted signal from an output terminal in accordance with the selection signal from said control circuit;

arranging a transfer line connected to an output of a register and an input of a selector of a flag register at one end of said array of said plurality of flag registers, and an output of a register and an input of a selector of a flag register at the other end;

connecting the output of said register in said flag register at said one end to said input terminal of said first 3-state inverter and further connecting the output from said output terminal to said selector in said flag register at said other end through said transfer line;

connecting the output of said register in said flag register at said other end to said input terminal of said second estate inverter and further connecting the output from said output terminal to said selector in said flag register at said one end through said transfer line; and in accordance with the selection signal from said control circuit, inputting an output from said register in said flag register at said one end to said selector in said flag register at said other end through said input terminal of said first 3-state inverter, said output terminal and said transfer line, and inverting and transferring the first or second data held by said register in said flag register at said one end to said selector in said flag register at said other end.

* * * * *

UNITED STATES PATENT AND TRADEMARK OFFICE
CERTIFICATE OF CORRECTION

PATENT NO. : 6,671,392 B1
DATED : December 30, 2003
INVENTOR(S) : Shigematsu et al.

It is certified that error appears in the above-identified patent and that said Letters Patent is hereby corrected as shown below:

Column 20,
Line 10, please delete "estate" and insert -- 3-state --.

Signed and Sealed this

Fifth Day of October, 2004

JON W. DUDAS
*Director of the United States Patent and Trademark Office*